United States Patent
Yuan et al.

(10) Patent No.: US 10,047,132 B2
(45) Date of Patent: *Aug. 14, 2018

(54) ERYTHROPOIETIN-DERIVED SHORT PEPTIDE AND ITS MIMICS AS IMMUNO/INFLAMMATORY MODULATORS

(71) Applicant: Peter C. Dowling, Fort Lee, NJ (US)

(72) Inventors: Rui Rong Yuan, Fort Lee, NJ (US);
Wei Ping Li, Kearny, NJ (US);
Yasuhiro Maeda, Belle Mead, NJ (US);
Peter C. Dowling, Fort Lee, NJ (US)

(73) Assignee: Peter C. Dowling, Fort Lee, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/703,457

(22) Filed: Sep. 13, 2017

(65) Prior Publication Data

US 2018/0016315 A1    Jan. 18, 2018

Related U.S. Application Data

(62) Division of application No. 14/161,931, filed on Jan. 23, 2014, now Pat. No. 9,765,128, which is a division of application No. 11/913,038, filed as application No. PCT/IB2006/003581 on May 1, 2006, now Pat. No. 8,653,028.

(60) Provisional application No. 60/676,592, filed on Apr. 29, 2005.

(51) Int. Cl.
*A61K 38/18* (2006.01)
*C07K 14/505* (2006.01)
*C07K 1/107* (2006.01)
*A61K 38/00* (2006.01)

(52) U.S. Cl.
CPC ............ *C07K 14/505* (2013.01); *A61K 38/00* (2013.01); *A61K 38/1816* (2013.01)

(58) Field of Classification Search
None
See application file for complete search history.

(56) References Cited

U.S. PATENT DOCUMENTS

| | | | |
|---|---|---|---|
| 4,105,027 A | 8/1978 | Lundquist |
| 4,192,309 A | 3/1980 | Poulsen |
| 4,227,522 A | 10/1980 | Carris |
| 4,627,432 A | 12/1986 | Newell |
| 4,778,054 A | 10/1988 | Newell |
| 4,811,731 A | 3/1989 | Newell |
| 5,035,237 A | 7/1991 | Newell |
| 5,350,695 A | 9/1994 | Colella |
| 5,986,047 A | 11/1999 | Wrighton |
| 6,531,121 B2 | 3/2003 | Brines |
| 6,831,060 B2 | 12/2004 | DeSauvage |
| 6,849,602 B1 | 2/2005 | O'Brien |
| 6,921,527 B2 | 7/2005 | Platz |
| 7,211,253 B1 | 5/2007 | Way |
| 7,410,941 B1 | 8/2008 | Brines et al. |
| 2004/0121958 A1 | 6/2004 | O'Brien |
| 2004/0171123 A1 | 9/2004 | Rosen |
| 2006/0035322 A1 | 2/2006 | Baker |
| 2007/0184519 A1 | 8/2007 | Tangri |
| 2009/0221482 A1 | 9/2009 | Cerami |
| 2009/0258821 A1 | 10/2009 | Cerami |
| 2011/0008363 A1 | 1/2011 | Meisel |
| 2011/0263504 A1 | 10/2011 | Cerami |

FOREIGN PATENT DOCUMENTS

| | | | |
|---|---|---|---|
| WO | WO 1991/016038 A1 | 10/1991 | |
| WO | WO-9424160 A2 * | 10/1994 | ........... C07K 14/505 |
| WO | WO 2004/108667 A2 | 12/2004 | |
| WO | WO-2007052154 A2 * | 5/2007 | ........... C07K 14/505 |

OTHER PUBLICATIONS

Abdul-Majid, et al., Comparing the pathogenesis of experimental autoimmune encephalomyelitis in CD4-/- and CD8-/- DBA/1 mice defines qualitative roles of different T cell subsets, J. Neuroimmunol. 141, pp. 10-19 (2003).
Battistini et al., CD8+ T cells from patients with acute multiple sclerosis display selective increase of adhesiveness in brain venules: a critical role for P-selectin glycoprotein ligand-1, Blood 101, pp. 2775-2782 (2003).
Bebo et al., Low-Dose Estrogen Therapy Ameliorates Experimental Autoimmune Encephalomyelitis in Two Different Inbred Mouse Strains, J. Immunol. 166, pp. 2080-2089 (2001).
Bernard et al., Myelin oligodendrite glycoprotein: a novel candidate authoantigen in multiple sclerosis, J. Mol. Med. 75, pp. 77-88 (1997).
Bettelli et al., Myelin Oligodendrocyte Glycoprotein-specific T Cell Receptor Transgenic Mice Development Spotaneious Autoimmune Optic Neuritis, J. Exp. Med. 197, pp. 1073-1081 (2003).
Belayev et al., Milddle cerebral artery occlusion in the mouse by intraluminal suture coated with poly-L-lysine: neurological and histological validation, Brain Res. 8933, pp. 181-190 (1999).
Brines, et al., Erythropoietin crosses the blood-brain barrier to protect against experimental brain injury, Proc. Nat'l. Acad. Sci. USA 97, pp. 10526-10531 (2000).
Brines, et al., Erythropoietin mediates tissue protectioh through an erythropoietin and common Beta-subunit heterorecptor, Proc. Nat'l. Acad. Sci. USA 101, 14907-14912 (2004).

(Continued)

*Primary Examiner* — Elizabeth C. Kemmerer
*Assistant Examiner* — Regina M DeBerry
(74) *Attorney, Agent, or Firm* — Nicholas R. Herrel; Locke Lord LLP

(57) ABSTRACT

The present disclosure provides isolated stabilized EPO-derived peptides and their mimics that protect against tissue damage in subjects having diverse forms of neural and non-neural organ system injury, pharmaceutical compositions containing the isolated stabilized EPO-derived peptides, methods for treating symptoms of a disease, disorder or condition having an inflammatory or an autoimmune component in a subject in need thereof, and methods for downregulating immune mediator activity in a subject in need thereof.

12 Claims, 12 Drawing Sheets

(56) References Cited

OTHER PUBLICATIONS

Brines, et al., Emerging biological roles for erythropoietin in the nervous system, Nature Reviews (Neuroscience) 6, pp. 484-494 (2005).
Buemi et al., The Pleiotropic Effects of Erythropoietin in the Central Nervous System, Neuropathol. Ex. Neurol. 62, pp. 228-236 (2003).
Buemi et al., Erythropoietin and the brain: from neurodevelopment to neuroprotection, Clin. Sci (Lond.) 103, pp. 275-282 (2002).
Campana et al., Identification of a neurotrophic sequence in erythropoietin, Inn J. Mol. Med. 1, pp. 235-241 (1998).
Crawford et al., High prevalance of autoreactive, neuroantigen-specific $CD8_+T$ cells in multiple sclerosis revealed by novel flow cytometric assay, Blood 103(11), pp. 4222-4231 (2004).
Engesser-Cesar et al., Voluntary Wheel Running Improves Recovery from a Moderate Spinal Cord Injury, J. Neurotrama 22, pp. 151-171 (2005).
Erbayraktar et al., Asialoerythropoietin is a nonerythropoietic cytokine with broad neuroprotective activity in vivo, Proc. Nat'l. Acad. Sci. USA 100, pp. 6741-6746 (2003).
Farooq et al. The in vivo and in vitro induction of anterior chamber associated immune deviation to myelin antigens in C57BL/6 mice. Brian, Behavior, and Immunity. 42: 118-122 (2014).
Ghosh et al., Transdermal & Tropical Drug Delivery Systems 249-97 (1997).
Habek et al. Pathology of Acute Disseminated Encephalomyelitis. Translational Neuroscience 2(3) 252-255 (2011).
Kirsch et al. EMBO J. BMP-2 antagonists emerge form alterations in the low affinity binding epitope for receptor BMPR-II. vol. 19(13): 3314-3324 (2000).
Leist et al., Derivatives of Erythropoietin That Are Tissue Protective but Not Erythropoietic, Science 305, pp. 239-242 (2004).
Li et al., Beneficial Effect of Erythropoietin on Experimental Allergic Encephalomyelitis, Ann. Neurol. 56. pp. 767-777 (2004).
Livnha, et al., Functional Mimicry of a Protein Hormone by a Peptide Agonist: The ERO Receptor Complex at 2.8 Angstroms, Science 273, pp. 464-471 (1996).
McColl, et al., Extension of cerebral hypopertusion and ischaemic pathology beyond MCA territory after intraluminal filament occlusion in C5761/6J mice, Brain Res. 997, pp. 14-22 (2004).
Mun, et al., Impaired Biological Activity of Erythropoietin Cyanate Carbamylation, Blood Purif. 18, pp. 13-17 (2000).
Ngo et al. Computational Complexity, Protein Structure Prediction and the Levinthal Paradox. The Protein Folding Problem and Tertiary Struncutre Prediction, pp. 433-440 and 492-495 (1994).
Sakanaka et al., In vivo evidence that erythropoietin protects neurons from ischemic damage, Proc. Nat'l Acad. Sci. USA 95 pp. 4635-4640 (1988).
Scheff, et al., Experimental Modeling of Spinal Cord Injury: Characterization of a Force-Defined Injury Device, J. Neurotrama 20, pp. 179-193 (2003).
Schindler et al., Transcriptional Responses to Polypeptide Ligands: The JAK STAT Pathway, Ann. Rev. Biochem. 64, pp. 621-651 (1995).
Siren et al., Erythropoietin—a novel concept for neuroprotection, Eur. Arch. Psychiatry Clin. Neurosci. 251, pp. 179-184 (2001).
Sobel et al., The Immunopathology of Chronic Experimental Allergic Encephalomyelitis Induced in Rabbits with Bovine Proteolipid Protein, J. Immunol. 136, pp. 157-163 (1986).
Trapp, et al., Pathogenesis of tissue injury in MS lesions, J. Neuroimmunol. 98. pp. 49-56 (1999).
Tsai et al., A Critical Role of Erythropoietin Receptor in Neurogenesis and Post-Stroke Recovery, J. Neurosci. 26, pp. 1269-1274 (2006).
Tuohy et al., Identification of an Encephalitogenic Determinant of Myelin Proteolipid Protein for SJL Mice, J. Immunol. 142, pp. 1523-1527 (1989).
Watowich et al., Activiation and Inhibition of Erythropoietin Receptor Function: Role of Receptor Dimerization, Mol. Cell Biol. 14, 3535-49 (1994).
Wells, J.A. Additivity of Mutational Effects in Proteins. Biochemistry, vol. 29, No. 37, pp. 8509-8517 (Sep. 18, 1990).
Wen, Erythropoietin Structure-Function Realtionships, J. Biol. Chem. 269, pp. 22839-22846 (1994).
Wrighton, et al., Small Peptides as Potent Mimetics of the Protein Hormone Erythropoietin, Science 273, pp. 458-463 (1996).
Yoshimura et al., Chronic Experimental Allergic Encephalomyelitis in Guinea Pigs Induced by Proteolipid Protein, J. Neurol. Sci. 69, pp. 47-58 (1985).
Wang, et al., "Beneficial effect of Erythropoietin short peptide on acute traumatic brain injury", Neurotherapies, 13: 418-427 (2016).
U.S. Appl. No. 14/161,931, filed Jan. 23, 2014, U.S. Pat. No. 9,765,128.
U.S. Appl. No. 11/913,038, filed Aug. 18, 2008, U.S. Pat. No. 8,653,028.

* cited by examiner

SEQUENCE LISTING

<160> NUMBER OF SEQ ID NOS: 32

<210> SEQ ID NO 1
<211> LENGTH: 20
<212> TYPE: PRT
<213> ORGANISM: Artificial

```
<220> FEATURE:
<223> OTHER INFORMATION: source: Isolated stabilized erythropoietin-
      derived peptide

<400> SEQUENCE: 1

Thr Thr Gly Cys Ala Glu His Cys Ser Leu Asn Glu Asn Ile Thr Val
1               5                   10                  15

Pro Asp Tyr Lys
            20

<210> SEQ ID NO 2
<211> LENGTH: 25
<212> TYPE: PRT
<213> ORGANISM: Artificial
<220> FEATURE:
<223> OTHER INFORMATION: source: isolated stabilized erythropoietin
      derived peptide

<400> SEQUENCE: 2

Ala Glu His Cys Ser Leu Asn Glu Asn Ile Thr Val Pro Asp Thr Lys
1               5                   10                  15

Val Asn Phe Tyr Ala Trp Arg Met Glu
            20                  25

<210> SEQ ID NO 3
<211> LENGTH: 18
<212> TYPE: PRT
<213> ORGANISM: Artificial
<220> FEATURE:
<223> OTHER INFORMATION: source: isolated stabilized erythropoietin
      derived peptide

<400> SEQUENCE: 3

Cys Ala Glu His Cys Ser Leu Asn Glu Asn Ile Thr Val Pro Asp Thr
1               5                   10                  15

Lys Val

<210> SEQ ID NO 4
<211> LENGTH: 17
<212> TYPE: PRT
<213> ORGANISM: Artificial
<220> FEATURE:
<223> OTHER INFORMATION: source: isolated stabilized erythropoietin
      derived peptide
<220> FEATURE:
<221> NAME/KEY: MISC_FEATURE
<223> OTHER INFORMATION: dBiotin is attached to the N-terminal amino
      acid

<400> SEQUENCE: 4

Ala Glu His Cys Ser Leu Asn Glu Asn Ile Thr Val Pro Asp Thr Lys
1               5                   10                  15

Val

<210> SEQ ID NO 5
<211> LENGTH: 6
<212> TYPE: PRT
<213> ORGANISM: Artificial
<220> FEATURE:
<223> OTHER INFORMATION: source: isolated stabilized erythropoietin
      derived peptide

<400> SEQUENCE: 5

Cys Ala Glu His Cys Ser
1               5
```

<210> SEQ ID NO 6
<211> LENGTH: 8
<212> TYPE: PRT
<213> ORGANISM: Artificial
<220> FEATURE:
<223> OTHER INFORMATION: source: isolated stabilized erythropoietin
      derived peptide

<400> SEQUENCE: 6

Gly Cys Ala Glu His Cys Ser Leu
1               5

<210> SEQ ID NO 7
<211> LENGTH: 19
<212> TYPE: PRT
<213> ORGANISM: Artificial
<220> FEATURE:
<223> OTHER INFORMATION: source: isolated stabilized erythropoietin
      derived peptide

<400> SEQUENCE: 7

Gly Cys Ala Glu His Cys Ser Leu Asn Glu Asn Ile Thr Val Pro Asp
1               5                   10                  15

Thr Lys Val

<210> SEQ ID NO 8
<211> LENGTH: 19
<212> TYPE: PRT
<213> ORGANISM: Artificial
<220> FEATURE:
<223> OTHER INFORMATION: source: isolated stabilized erythropoietin
      derived peptide
<220> FEATURE:
<221> NAME/KEY: MISC_FEATURE
<223> OTHER INFORMATION: dBiotin is attached to N-terminal amino acid

<400> SEQUENCE: 8

Gly Cys Ala Glu His Cys Ser Leu Asn Glu Asn Ile Thr Val Pro Asp
1               5                   10                  15

Thr Lys Val

<210> SEQ ID NO 9
<211> LENGTH: 14
<212> TYPE: PRT
<213> ORGANISM: Artificial
<220> FEATURE:
<223> OTHER INFORMATION: source: isolated stabilized erythropoietin
      derived peptide

<400> SEQUENCE: 9

Cys Ala Glu His Cys Ser Leu Asn Glu Asn Ile Thr Val Pro
1               5                   10

<210> SEQ ID NO 10
<211> LENGTH: 13
<212> TYPE: PRT
<213> ORGANISM: Artificial
<220> FEATURE:
<223> OTHER INFORMATION: source: isolated stabilized erythropoietin
      derived peptide
<220> FEATURE:
<221> NAME/KEY: MISC_FEATURE
<223> OTHER INFORMATION: dBiotin is attached to N-terminal amino acid

<400> SEQUENCE: 10

Ala Glu His Cys Ser Leu Asn Glu Asn Ile Thr Val Pro
1               5                   10

<210> SEQ ID NO 11
<211> LENGTH: 21
<212> TYPE: PRT
<213> ORGANISM: Artificial
<220> FEATURE:
<223> OTHER INFORMATION: source: isolated stabilized erythropoietin
      derived peptide

<400> SEQUENCE: 11

Thr Thr Gly Cys Ala Glu His Cys Ser Leu Asn Glu Asn Ile Thr Val
1               5                   10                  15

Pro Asp Thr Lys Val
            20

<210> SEQ ID NO 12
<211> LENGTH: 17
<212> TYPE: PRT
<213> ORGANISM: Artificial
<220> FEATURE:
<223> OTHER INFORMATION: source: isolated stabilized erythropoietin
      derived peptide

<400> SEQUENCE: 12

Thr Thr Gly Cys Ala Glu His Cys Ser Leu Asn Glu Asn Ile Thr Val
1               5                   10                  15

Pro

<210> SEQ ID NO 13
<211> LENGTH: 13
<212> TYPE: PRT
<213> ORGANISM: Artificial
<220> FEATURE:
<223> OTHER INFORMATION: source: isolated stabilized erythropoietin
      derived peptide

<400> SEQUENCE: 13

Ser Leu Asn Glu Asn Ile Thr Val Pro Asp Thr Lys Val
1               5                   10

<210> SEQ ID NO 14
<211> LENGTH: 17
<212> TYPE: PRT
<213> ORGANISM: Artificial
<220> FEATURE:
<223> OTHER INFORMATION: source: isolated stabilized erythropoietin
      derived peptide
<220> FEATURE:
<221> NAME/KEY: MISC_FEATURE
<223> OTHER INFORMATION: biotin attached to C-terminal amino acid

<400> SEQUENCE: 14

Ala Glu His Cys Ser Leu Asn Glu Asn Ile Thr Val Pro Asp Thr Lys
1               5                   10                  15

Lys

<210> SEQ ID NO 15
<211> LENGTH: 25
<212> TYPE: PRT
<213> ORGANISM: Artificial
<220> FEATURE:
<223> OTHER INFORMATION: source: isolated stabilized erythropoietin
      derived peptide

<400> SEQUENCE: 15

Cys Ala Glu His Cys Ser Leu Lys His Gln Gly Leu Asn Lys Asn Ile

```
1               5                  10                  15
Asn Leu Asp Ser Val Asp Gly Val Pro
            20                  25

<210> SEQ ID NO 16
<211> LENGTH: 25
<212> TYPE: PRT
<213> ORGANISM: Artificial
<220> FEATURE:
<223> OTHER INFORMATION: source: isolated stabilized erythropoietin
      derived peptide
<220> FEATURE:
<221> NAME/KEY: MISC_FEATURE
<223> OTHER INFORMATION: dBiotin attached to N-terminal amino acid

<400> SEQUENCE: 16

Cys Ala Glu His Cys Ser Leu Lys His Gln Gly Leu Asn Lys Asn Ile
1               5                  10                  15
Asn Leu Asp Ser Val Asp Gly Val Pro
            20                  25

<210> SEQ ID NO 17
<211> LENGTH: 18
<212> TYPE: PRT
<213> ORGANISM: Artificial
<220> FEATURE:
<223> OTHER INFORMATION: source: isolated stabilized erythropoietin
      derived peptide

<400> SEQUENCE: 17

Gly Cys Ala Glu His Cys Ser Leu Met Glu Asn Asn Leu Arg Arg Pro
1               5                  10                  15
Asn Leu

<210> SEQ ID NO 18
<211> LENGTH: 18
<212> TYPE: PRT
<213> ORGANISM: Artificial
<220> FEATURE:
<223> OTHER INFORMATION: source: isolated stabilized erythropoietin
      derived peptide
<220> FEATURE:
<221> NAME/KEY: MISC_FEATURE
<223> OTHER INFORMATION: dBiotin attached to N-terminal amino acid

<400> SEQUENCE: 18

Gly Cys Ala Glu His Cys Ser Leu Met Glu Asn Asn Leu Arg Arg Pro
1               5                  10                  15
Asn Leu

<210> SEQ ID NO 19
<211> LENGTH: 12
<212> TYPE: PRT
<213> ORGANISM: Artificial
<220> FEATURE:
<223> OTHER INFORMATION: source: isolated stabilized erythropoietin
      derived peptide
<220> FEATURE:
<221> NAME/KEY: MISC_FEATURE
<223> OTHER INFORMATION: dBiotin attached to N-terminal amino acid

<400> SEQUENCE: 19

Ile Leu Met Glu Asn Asn Leu Arg Arg Pro Asn Leu
1               5                  10

<210> SEQ ID NO 20
```

```
<211> LENGTH: 16
<212> TYPE: PRT
<213> ORGANISM: Artificial
<220> FEATURE:
<223> OTHER INFORMATION: source: isolated stabilized erythropoietin
      derived peptide
<220> FEATURE:
<221> NAME/KEY: MISC_FEATURE
<223> OTHER INFORMATION: dBiotin attached to N-terminal amino acid

<400> SEQUENCE: 20

Ala Glu His Cys Ser Leu Met Glu Asn Asn Leu Arg Arg Pro Asn Leu
1               5                   10                  15

<210> SEQ ID NO 21
<211> LENGTH: 17
<212> TYPE: PRT
<213> ORGANISM: Artificial
<220> FEATURE:
<223> OTHER INFORMATION: source: isolated stabilized erythropoietin
      derived peptide

<400> SEQUENCE: 21

Ala Glu His Cys Ser Leu Asn Glu Asn Ile Thr Val Pro Asp Thr Lys
1               5                   10                  15

Val

<210> SEQ ID NO 22
<211> LENGTH: 21
<212> TYPE: PRT
<213> ORGANISM: Artificial
<220> FEATURE:
<223> OTHER INFORMATION: source: isolated stabilized erythropoietin
      derived peptide

<400> SEQUENCE: 22

Met Glu Val Gly Trp Tyr Arg Ser Pro Phe Ser Arg Val Val His Leu
1               5                   10                  15

Tyr Arg Asn Gly Lys
            20

<210> SEQ ID NO 23
<211> LENGTH: 15
<212> TYPE: PRT
<213> ORGANISM: Artificial
<220> FEATURE:
<223> OTHER INFORMATION: source: isolated stabilized erythropoietin
      derived peptide

<400> SEQUENCE: 23

Tyr Arg Ser Pro Phe Ser Arg Val Val His Leu Tyr Arg Asn Gly
1               5                   10                  15

<210> SEQ ID NO 24
<211> LENGTH: 11
<212> TYPE: PRT
<213> ORGANISM: Artificial
<220> FEATURE:
<223> OTHER INFORMATION: source: isolated stabilized erythropoietin
      derived peptide

<400> SEQUENCE: 24

Phe Ser Arg Val Val His Leu Tyr Arg Asn Gly
1               5                   10

<210> SEQ ID NO 25
<211> LENGTH: 13
```

```
<212> TYPE: PRT
<213> ORGANISM: Artificial
<220> FEATURE:
<223> OTHER INFORMATION: source: isolated stabilized erythropoietin

```
<223> OTHER INFORMATION: source: isolated stabilized erythropoietin
      derived peptide

<400> SEQUENCE: 30

Ala Glu His Cys Ser Leu Met Glu Asn Asn Leu Arg Arg Pro Asn Leu
1               5                   10                  15

<210> SEQ ID NO 31
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid residue with a sulfhydral group
<220> FEATURE:
<221> NAME/KEY: MISC_FEATURE
<222> LOCATION: (5)..(5)
<223> OTHER INFORMATION: Amino acid residue with a sulfhydral group

<400> SEQUENCE: 31

Xaa Ala Glu His Xaa Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Amino acid residue with a sulfhydral group
<220> FEATURE:
<221> NAME/KEY: MISC_FEATURE
<222> LOCATION: (7)..(7)
<223> OTHER INFORMATION: Amino acid residue with a sulfhydral group

<400> SEQUENCE: 32

Ala Glu His Xaa Ser Leu Xaa
1               5
```

ERYTHROPOIETIN-DERIVED SHORT PEPTIDE AND ITS MIMICS AS IMMUNO/INFLAMMATORY MODULATORS

CROSS-REFERENCE TO RELATED APPLICATIONS

This application is a Divisional application of U.S. patent application Ser. No. 14/161,931, filed 23 Jan. 2014, and U.S. patent application Ser. No. 11/913,038, filed 18 Aug. 2008, and now U.S. Pat. No. 8,653,028, which is a National Stage application of PCT/IB2006/003581, filed 1 May 2006, and which claims priority to U.S. provisional application No. 60/676,592, filed 29 Apr. 2005, all of which are incorporated by reference herein in their entireties for all purposes.

INCORPORATION BY REFERENCE

In compliance with 37 C.F.R. § 1.52(e)(5), the sequence information contained in electronic file name: 1513191_100US53_Sequence_Listing_22AUG2017_ST25.txt; size 10.3 KB, created on 22 Aug. 2017, using Patent-In 3.5, and Checker 4.4.0 is hereby incorporated herein by reference in its entirety.

FIELD OF THE INVENTION

The present invention relates to erythropoietin-derived short peptides and their mimics that protect against tissue damage in animals having diverse forms of neural and non-neural organ system injury.

BACKGROUND OF THE INVENTION

Erythropoietin and its Non-Hematopoietic Activities

Erythropoietin (EPO), a 165 amino acid glycoprotein hormone, was identified initially as a hematopoietic growth factor and has been used extensively for the treatment of anemia in humans. Whole molecule EPO received considerable attention recently because it may have broad neuroprotective capabilities following CNS injury [Brines, M. L., et al., Proc Natl Acad Sci USA, 97: 10526-31 (2000); Siren, A. L. and Ehrenreich, H., Eur Arch Psychiatry Clin Neurosci, 251: 179-84 (2001); Buemi, M., et al., J. Neuropathol Exp Neurol, 62: 228-36 (2003); Li, W., et al., Ann Neurol, 56: 767-77 (2004); Sakanaka, M., et al., Proc Natl Acad Sci USA, 95: 4635-40 (1998)]. Therapeutic effects of exogenously administered EPO on several diverse forms of neurologic injury, including occlusive cerebral vascular disease, acute brain trauma, epilepsy, and an autoimmune model of demyelinating disease, experimental autoimmune encephalomyelitis (EAE), have been tested and the degree of neurologic impairment was significantly reduced [(Brines, M. L. et al., Proc Natl Acad Sci USA, 97: 10526-31 (2000); Li, W. et al., Ann Neurol, 56: 767-77 (2004); Tsai, P. T., et al., J Neurosci, 26: 1269-74 (2006); Buemi, M., et al., Clin Sci (Land), 103: 275-82 (2002)]. However, long-term EPO therapy remains significantly limited in non-anemic patients with neurological injury because EPO treatment may overly stimulate erythropoiesis. To overcome this concern, EPO therapy would have to be limited to very short term use. Other EPO molecular preparations, such as an asialo-form of EPO, carbamylated EPO (CEPO), or certain EPO mutants, have been shown to be neuroprotective in animals following experimental traumatic spinal cord injury or acute stroke without provoking an increase in red cell mass [Erbayraktar, S., et al., Proc Natl Acad Sci USA, 100: 6741-46 (2003); Leist, M., et al., Science, 305: 239-42 (2004); Mun, K. C. and Go!per, T. A. Blood Purif, 18: 13-17 (2000); Brines, M., et al., Proc Natl Acad Sci USA, 101: 14907-12 (2004). A short 17 amino acid EPO-derived linear peptide also was reported to have neuroprotective effects in cell culture, but its in vivo biologic effects were not certain [Campana, W. M., et al., Intl J Mol Med, 1: 235-41 (1998). Taken all together, the evidence suggests that specific functional and structural domains may co-exist within the full 165 amino acid EPO molecule.

The hematopoietic effect of EPO is mediated by binding and inducing dimerization of two molecules of the EPO receptor (EpoR) on the cell surface [Watowich, S. S., et al., Mol Cell Biol, 14: 3535-49 (1994)]. The EpoR belongs to a cytokine receptor superfamily that is also related to the cytokines granulocyte colony-stimulating factor (G-CSF), granulocyte macrophage colony-stimulating factor (GM-CSF), interleukins 2-7 and ciliary neurotrophic factor (CNTF). The signaling pathway involves the autophosphorylation and activation of the Janus family protein tyrosine kinase, JAK-2, which further activates additional signaling proteins including STATS, Ras-mitogen-activated protein kinase (MAPK) and phosphatidylinositol 3-kinase (PI3K). Studies on structure activity relationships of EPO have identified regions and amino acids essential for binding to the erythropoietin receptor (EpoR) [Livnah, O., et al., Science, 273: 464-71 (1996); Wrighton, N. C., et al., Science, 273: 458-64 (1996); Wen, D., J Biol Chem, 269: 22839-46 (1994)]. Studies in which recombinant EPO and EPO mutants have been tested for their biological effects in a variety of animal models have suggested that the neuroprotection mediated by EPO might not occur through a conventional interaction between EPO and classic EpoR. The common β receptor (βcR) or CD131, which is also an important component for other ligands including IL-3, IL-5 and GM-CSF, has been proposed to be a key subunit associated with the EpoR that is responsible for EPO mediated non-hematopoietic effects. Additional unknown receptor(s) also may play critical roles in the non-hematopoietic effects induced by chemically modified or mutant EPO. Based on the belief that there are at least two distinct functional peptide domains co-existing within the whole EPO molecule and that sequences and/or structures within the EPO-derived peptides will dictate their biological functions, small EPO-derived peptides with different biological functions having neuroprotective and immunomodulatory activity have been identified and characterized herein.

EAE Animal Model and Multiple Sclerosis

Multiple sclerosis (MS) a disorder of unknown cause, is defined clinically by characteristic symptoms, signs and progression, and is defined pathologically by scattered areas of inflammation and demyelination affecting the brain, optic nerves and spinal cord white matter. It is widely believed that the pathogenesis of MS involves an immune-mediated inflammatory demyelinating process.

Experimental autoimmune encephalomyelitis (EAE) is a central nervous system inflammatory demyelinating disease involving acute injury to the brain and spinal cord white matter. This animal model has been used widely by many investigators to study disease pathogenesis and to explore new therapies for its human counterpart, multiple sclerosis (MS). Pathogenesis of both MS and EAE is believed to involve (1) activation of myelin reactive T cells; (2) upregulated expression of chemokines and adhesion molecules; (3) focal T cells and macrophage infiltration into the CNS white matter; and (4) demyelination and axonal injury and loss of neurological function [Trapp., B. et al., J Neuroimmunol, 98:

49-56 (1999)]. In both EAE and MS, activated T-lymphocytes specific for self-antigens present in myelin are linked to CNS inflammation and to the breakdown of the blood brain barrier to peripheral blood leukocytes and plasma proteins; this is predominantly restricted to myelin rich white matter area of the CNS [Bettelli, E., et al., J Exp Med, 197: 1073-81 (2003); Crawford, M. P., et al., Blood 103(11): 4222-31 (2004); Abdul-Majid, K. B., et al., J Neuroimmunol, 141: 10-19 (2003); Battistini, L., et al., Blood, 101: 4775-82 (2003).

EAE can be induced experimentally in genetically susceptible animals, such as mice, by immunization with immunodominant peptides from myelin proteins, such as myelin basic protein (MBP), proteolipid protein (PLP), and myelin oligodendrocytes glycoprotein (MOG), emulsified in complete Freund's adjuvant followed by injection of pertussis toxin as an additional adjuvant for certain mouse strains [Li, W., et al., Ann Neurol, 56: 767-77 (2004). Disease development is variable from strain to strain. For example, in SJL/J mice, PLP or MBP induces a relapsing-remitting progression, whereas C57BL/6 mice immunized with MOG often develop a chronic form of disease.

A library of stabilized isolated EPO-derived peptides comprising about 7 to about 25 amino acids in length has been created and tested in vitro and in vivo for therapeutic efficacy. It has been shown that these short EPO-derived peptides are highly protective in mouse models of EAE, acute stroke, acute spinal cord and brain injury as well as arthritis by reversing and/or reducing manifestations of the associated disease. This protection is maintained during long term observation in EAE mice and was not associated with hematological side effects. These short peptides protect against tissue damage by modulating the immune-mediated inflammatory network, i.e. by reducing major histocompatibilty complex (MHC) class I and class II over-expression; by reducing inflammatory cytokines; and by suppressing antigen-specific T cell function in peripheral lymphoid tissue and brain tissue as well as in in vitro tissue culture assays. The peptide domain that is crucial for immunomodulating/anti-inflammation functions as well as a small peptide ring that plays an important role in maintaining the stability, without hampering biologic efficacy, of these small peptides have been identified. Moreover, addition of a small bicyclic compound, such as d-biotin, to the N- or C-terminal of linear cytokine-derived peptides, including, but not limited to, short EPO linear peptides, the stability of these peptides is increased without hampering their biologic activity. These newly developed small peptides hold immense potential for direct clinical application in treatment of central and peripheral nervous system diseases associated with injury including demyelinating diseases, traumatic injury and stroke. Since the beneficial effect of these peptides is not limited to neural tissue organs, they are broadly useful in the treatment of inflammatory/immune injury to non-neural organs of the body.

SUMMARY OF THE INVENTION

The present invention provides stabilized, isolated EPO-derived peptides and their mimics that protect against tissue damage in subjects having diverse forms of neural and non-neural organ system injury, pharmaceutical compositions containing the isolated EPO-derived peptides, methods for treating symptoms of a disease, disorder or condition having an inflammatory or an autoimmune component in a subject in need thereof, and methods for downregulating immune mediator activity in a subject in need thereof. In one embodiment of the present invention, a stabilized isolated EPO-derived peptide comprises an amino acid sequence comprising an N-terminal end and a C-terminal end and having a non-hematopoietic biological activity, wherein the non-hematopoietic biological activity of the stabilized EPO-derived peptide is stable when the peptide is stored at 4° C. In another embodiment, this EPO-derived peptide is stabilized by chemically adding a small bicyclic molecule to at least one of the N-terminal end or the C-terminal end of the peptide's amino acid sequence. In another embodiment, this stabilized isolated EPO-derived peptide is at least one peptide whose amino acid sequence is selected from the group consisting of SEQ ID NO: 4, SEQ ID NO: 10, SEQ ID NO: 14, and SEQ ID NO: 27. In another embodiment, the stabilized, isolated EPO-derived peptide is stabilized by a disulfide bond formed between a sulfhydral group of a first amino acid residue and a sulfhydral group of a second amino acid residue along the peptide sequence. In another embodiment, the stabilized, isolated EPO-derived peptide comprises at least 6 amino acids having the peptide sequence XAEHYS (SEQ ID NO: 31), wherein X is a first amino acid residue containing a sulfhydral group and Y is a second amino acid residue containing a sulfhydral group, and wherein the sulfhydral group of the first amino acid residue is at an appropriate distance from the sulfhydral group of the second amino acid residue to form the disulfide bond with the sulfhydral group of the second amino acid residue within the peptide sequence, thus stabilizing the peptide. In another embodiment, the disulfide-bond-stabilized, isolated EPO-derived peptide is at least one peptide whose amino acid sequence is selected from the group consisting of SEQ ID NO: 1, SEQ ID NO: 3, SEQ ID NO: 5, SEQ ID NO: 6, SEQ ID NO: 7, SEQ ID NO: 9, SEQ ID NO: 11, SEQ ID NO: 12, and SEQ ID NO: 15. In another embodiment, the disulfide bond-stabilized isolated EPO-derived peptide is further stabilized by chemically adding a small bicyclic molecule to at least one of the N-terminal end or the C-terminal end of the peptide's amino acid sequence. In yet another embodiment, the EPO-derived peptide comprises at least 7 amino acids having the peptide sequence XAEHYS (SEQ ID NO: 31), wherein X is a first amino acid residue containing a sulfhydral group and Y is a second amino acid residue containing a sulfhydral group, and wherein the sulfhydral group of the first amino acid residue is at an appropriate distance from the sulfhydral group of the second amino acid residue to form the disulfide bond with the sulfhydral group of the second amino acid residue within the peptide sequence, thus stabilizing the peptide. In another embodiment, this disulfide bond-stabilized isolated EPO-derived peptide is at least one peptide whose amino acid sequence is selected from the group consisting of SEQ ID NO: 30. In another embodiment, this disulfide bond-stablized EPO-derived peptide is further stabilized by chemically adding a small bicyclic molecule to at least one of the N-terminal end or the C-terminal end of the peptide's amino acid sequence. In another embodiment, the disulfide bond-stabilized EPO-derived peptide further stabilized by chemically adding a small bicyclic molecule is at least one peptide whose amino acid sequence is SEQ ID NO: 20. In yet another embodiment, the isolated stabilized EPO-derived peptide mimics the non-hematopoietic biological activity of at least one peptide whose amino acid sequence is selected from the group consisting of SEQ ID NO: 1, SEQ ID NO: 3, SEQ ID NO: 4; SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 14, SEQ ID NO: 15, SEQ ID NO: 17, SEQ ID NO: 18, SEQ ID NO: 20, SEQ ID NO: 27, AND SEQ ID NO: 30.

The present invention further provides a pharmaceutical composition for treating symptoms of a disease, disorder or condition having an inflammatory or autoimmune component in a subject in need thereof comprising a therapeutically effective amount of at least one stabilized isolated EPO-derived peptide, wherein the animals' red cell indices remain substantially at normal levels during treatment. In one embodiment, the disease, disorder or condition having an inflammatory or autoimmune component is at least one disease, disorder or condition selected from the group consisting of immune-mediated inflammation, an autoimmune disease, a demyelinating disease, an arthritis, an acute cerebrovascular injury, an acute spinal cord injury, an acute brain injury, and an acute cardiovascular injury. In another embodiment, the stabilized EPO-derived peptide of the composition comprises an amino acid sequence comprising an N-terminal end and a C-terminal end and has a non-hematopoietic biological activity, wherein the non-hematopoietic biological activity of the stabilized EPO-derived peptide is stable when the peptide is stored at 4° C. In another embodiment, the isolated stabilized EPO-derived peptide is stabilized by chemically adding a small bicyclic molecule to at least one of the N-terminal end or the C-terminal end of the peptide's amino acid sequence. In another embodiment, the isolated stabilized EPO-derived peptide of the composition is at least one peptide whose amino acid sequence is selected from the group consisting of SEQ ID NO: 4, SEQ ID NO: 10, SEQ ID NO: 14, and SEQ ID NO: 27. In another embodiment, the stabilized EPO-derived peptide of the composition is stabilized by a disulfide bond formed between a sulfhydral group of a first amino acid residue and a sulfhydral group of a second amino acid residue along the peptide sequence. In another embodiment, the stabilized isolated EPO-derived peptide of the composition comprises at least 6 amino acids having the peptide sequence XAEHYS (SEQ ID NO: 31), wherein X is a first amino acid residue containing a sulfhydral group and Y is a second amino acid residue containing a sulfhydral group, and wherein the sulfhydral group of the first amino acid residue is at an appropriate distance from the sulfhydral group of the second amino acid residue to form the disulfide bond with the sulfhydral group of the second amino acid residue within the peptide sequence, thus stabilizing the peptide. In another embodiment, the isolated disulfide bond-stabilized EPO-derived peptide is at least one peptide whose amino acid sequence is selected from the group consisting of SEQ ID NO: 1, SEQ ID NO; 3, SEQ ID NO: 5, SEQ ID NO: 6, SEQ ID NO: 7, SEQ ID NO: 9, SEQ ID NO: 11, SEQ ID NO: 12, and SEQ ID NO: 15. In another embodiment, the isolated stabilized EPO-derived peptide of the composition comprises at least 7 amino acids having the peptide sequence XAEHYS (SEQ ID NO: 31), wherein X is a first amino acid residue containing a sulfhydral group and Y is a second amino acid residue containing a sulfhydral group, and wherein the sulfhydral group of the first amino acid residue is at an appropriate distance from the sulfhydral group of the second amino acid residue to form the disulfide bond with the sulfhydral group of the second amino acid residue within the peptide sequence, thus stabilizing the peptide. In another embodiment, the isolated disulfide bond-stabilized EPO-derived peptide of the composition is at least one peptide whose amino acid sequence is SEQ ID NO: 30. In another embodiment, the isolated disulfide-bond stabilized EPO-derived peptide of the composition is further stabilized by chemically adding a small bicyclic molecule to at least one of the N-terminal end or The C-terminal end of the peptide's amino acid sequence. In another embodiment, the isolated disulfide bond-stabilized EPO-derived peptide further stabilized by chemically adding the small bicyclic molecule lis at least one peptide whose amino acid sequence is SEQ ID NO: 20. In another embodiment, the isolated stabilized EPO-derived peptide of the composition mimics the non-hematopoietic biological activity of at least one peptide whose amino acid sequence is selected from the group consisting of SEQ ID NO: 1, SEQ ID NO: 3, SEQ ID NO: 4; SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 14, SEQ ID NO: 15, SEQ ID NO: 17, SEQ ID NO: 18, SEQ ID NO: 20, SEQ ID NO; 27 AND SEQ ID NO: 30. In another embodiment, the composition is administered by a route selected from the group consisting of orally, buccally, parenterally, nasally, rectally, and topically.

In addition, the present invention provides a method of treating symptoms of a disease, disorder or condition having an inflammatory or autoimmune component in a subject in need thereof, the method comprising the steps: (a) administering to the subject a therapeutically effective amount of a composition comprising at least one stabilized isolated EPO-derived peptide comprising an amino acid sequence comprising an N-terminal end and a C-terminal end and having a non-hematopoietic biological activity; (b) monitoring the subject's red blood cell indices; and (c) maintaining the subject's red cell indices at substantially normal levels during treatment. In one embodiment of the method, the non-hematopoietic biological activity of the stabilized isolated EPO-derived peptide is stable when the peptide is stored at 4° C. In another embodiment of the method, the isolated stabilized EPO-derived peptide is stabilized by chemically adding a small bicyclic molecule to at least one of the N-terminal end or the C-terminal end of the peptide's amino acid sequence. In another embodiment of the method, the isolated stabilized EPO-derived peptide is at least one peptide whose amino acid sequence is selected from the group consisting of SEQ ID NO: 4, SEQ ID NO: 10, SEQ ID NO: 14, and SEQ ID NO: 27. In another embodiment of the method, the stabilized isolated EPO-derived peptide is stabilized by a disulfide bond formed between a sulfhydral group of a first amino acid residue and a sulfhydral group of a second amino acid residue along the peptide sequence. In another embodiment of the method, the isolated stabilized EPO-derived peptide comprises at least 6 amino acids having the peptide sequence XAEHYS (SEQ ID NO: 31), wherein X is a first amino acid residue containing a sulfhydral group and Y is a second amino acid residue containing a sulfhydral group, and wherein the sulfhydral group of the first amino acid residue is at an appropriate distance from the sulfhydral group of the second amino acid residue to form the disulfide bond with the sulfhydral group of the second amino acid residue within the peptide sequence, thus stabilizing the peptide. In another embodiment of the method, the isolated disulfide bond-stabilized EPO-derived peptide is at least one peptide whose amino acid sequence is selected from the group consisting of SEQ ID NO: 1, SEQ ID NO; 3, SEQ ID NO: 5, SEQ ID NO: 6, SEQ ID NO: 7, SEQ ID NO: 9, SEQ ID NO: 11, SEQ ID NO: 12, and SEQ ID NO: 15. In another embodiment of the method, the isolated disulfide bond-stabilized EPO-derived peptide is further stabilized by chemically adding a small bicyclic molecule to at least one of the N-terminal end or the C-terminal end of the peptide's amino acid sequence. In another embodiment of the method, the isolated stabilized EPO-derived peptide comprises at least 7 amino acids having the peptide sequence XAEHYS (SEQ ID NO: 31), wherein X is a first amino acid residue containing a sulfhydral group and Y is a second amino acid residue containing a sulfhydral group, and wherein the sulfhydral group of the first amino acid residue is at an appropriate distance from the sulfhydral group of the second amino acid residue to form the disulfide bond with the sulfhydral group of the second amino acid residue within the peptide sequence, thus stabilizing the peptide. In another embodiment of the method, the isolated disulfide bond-stabilized EPO-derived peptide is at least one peptide whose amino acid sequence is SEQ ID NO: 30. In another embodiment of the method, the isolated stabilized EPO-derived peptide is further stabilized by chemically adding a small bicyclic molecule to at least one of the N-terminal end or the C-terminal end of the peptide's amino acid sequence. In another embodiment of the method, the isolated disulfide bond-stabilized EPO-derived peptide is at least one peptide whose amino acid sequence is SEQ ID NO: 20. In another embodiment of the method, the isolated stabilized EPO-derived peptide mimics the non-hematopoetic biological activity of at least one peptide whose amino acid sequence is selected from the group consisting of SEQ ID NO: 1, SEQ ID NO; 3, SEQ ID NO: 4; SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 17, SEQ ID NO: 18, SEQ ID NO: 20 AND SEQ ID NO: 30. In yet another embodiment of the method, when administered in a therapeutically effective amount to a subject in need thereof, the stabilized isolated EPO-derived peptide reduces clinical symptoms of at least one disease, disorder, or condition having an inflammatory or autoimmune component selected from the group consisting of an acute cerebrovascular injury, an acute spinal cord injury, an acute brain injury, an acute cardiovascular injury, an arthritis, an autoimmune disease, a demyelinating disease, and immune-mediated inflammation. In still another embodiment, the composition is administered by a route selected from the group consisting of orally, buccally, parenterally, nasally, rectally, and topically.

DETAILED DESCRIPTION OF THE INVENTION

Figure 1:
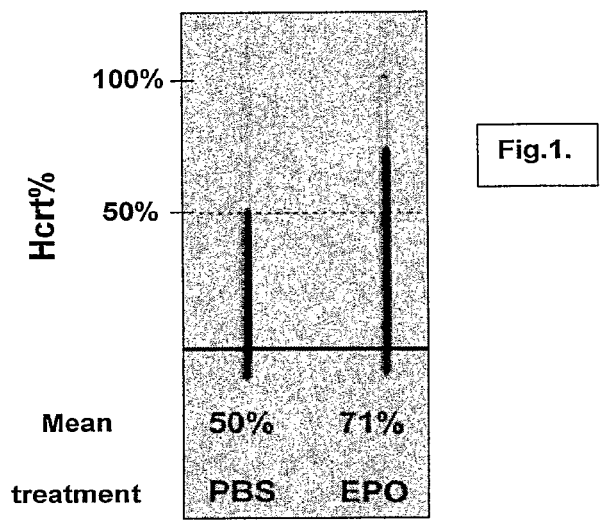
FIG. 1 shows that whole EPO increases the hematocrit level in SJL/J mice.

In one aspect, the present invention provides pharmaceutical compositions for treating symptoms of an inflammatory disease, disorder or condition in a subject comprising a therapeutically effective amount of at least one Epo-AB loop peptide, and a pharmaceutically acceptable carrier, wherein the animals' red cell indices remain substantially at normal levels during treatment. A "pharmaceutical composition" is one that is employed to prevent, reduce in intensity, cure, or otherwise treat a target condition, syndrome, disorder or disease that has undergone federal regulatory review.

The term "disease" or "disorder", as used herein, refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition", as used herein, refers to a variety of health states and is meant to include disorders or diseases caused by any underlying mechanism or disorder, injury, and the promotion of healthy tissues and organs.

In another aspect, the present invention provides methods of treating symptoms of an inflammatory disease, disorder or condition in a subject, the methods comprising the step of administering to the subject a therapeutically effective amount of at least one stabilized Epo-AB loop peptide; monitoring the subject's red blood cell indices; and maintaining the subject's red cell indices substantially at normal levels during treatment. In yet another aspect, the present invention provides methods for downregulating immune mediator activity in a subject in vivo, the methods comprising the steps of administering to the subject a therapeutically effective amount of at least one Epo-AB loop peptide; monitoring the subject's red blood cell indices; and maintaining the subject's red cell indices substantially at normal levels during treatment.

The term "glial filament acidic protein" (GFAP) as used herein refers to an intermediate filament protein predominantly expressed in cells of astroglial origin, which is a marker for astrocytes.

The term "active" refers to the ingredient, component or constituent of the compositions of the present invention responsible for the intended therapeutic effect.

The term "astrocyte" as used herein refers to relatively large glial cells with threadlike projections that connect with neurons and small blood vessels (capillaries). These projections form part of the so-called "blood-brain barrier." Astrocytes also accumulate in areas where nerves have been damaged (astrocytosis), sealing off these areas. An excess of astrocytes in damaged areas of the CNS is known as gliosis.

As used herein, the term "autoimmune" refers to an immune response against a subject's own tissues or organs. Autoimmune disorders result from abnormal immune reactions in which the actions of certain white blood cells (T cells) are directed against "self proteins" (autoantigens) or normal tissue components (i.e., cell-mediated immune response)—or in which specialized proteins (antibodies) produced in response to specific, usually foreign proteins (antigens) improperly act against certain of the body's own cells (i.e., antibody-mediated immune response). The autoimmune process may be primarily directed against one organ, such as the thyroid gland in Hashimoto's thyroiditis or the pancreas in insulin-dependent diabetes mellitus, or may involve multiple organs and bodily systems, such as associated with systemic lupus erythematosus (lupus or SLE).

"Biotin" as used herein refers to a small bicyclic molecule that binds with high affinity to avidin and streptavidin. Biotin is used to label nucleic acids and proteins that may be subsequently detected by avidin or streptavidin linked to a fluorescent or enzymatic reporter molecule.

The terms "blood brain barrier" or "blood-CSF barrier" are used interchangeably to describe systems for excluding substances from the brain and for transporting substances from blood to CSF or brain and vice versa to preserve homeostasis in the nervous system. The barriers facilitate entry of necessary metabolites, but block entry or facilitate removal of unnecessary metabolites or toxic substances. For any solute (i.e., a substance dissolved in and by a solvent), the efficacy of the exclusion or the transport is determined by morphological and functional characteristics of the brain and spinal cord capillaries and by the biochemical and biophysical characteristics of the solute. The barrier systems include carrier-mediated transport systems. Lipid solubility also enhances the transport of substances; thus, ionized polar compounds enter the brain slowly unless there is a specific transport system for them.

The term "central nervous system" (CNS) as used herein refers to the brain and spinal cord.

The term "cerebrovascular injury" as used herein refers to an injury of, pertaining to, or affecting blood vessels in and to the brain.

The term "cardiovascular injury" as used herein refers to an injury of, pertaining to, or affecting the heart and blood vessels.

The term "chemokine" as used herein refers to a class of chemotactic cytokines that signal leukocytes to move in a specific direction.

The term "cytokine" as used herein refers to a soluble messenger substance secreted by a cell that acts on specific cytokine receptors and affects the behavior of target cells. For example, lymphokines, chemokines, interferons, colony stimulating factors, and tumor necrosis factors are cytokines. Cytokines have been implicated in the regulation of the immune response in inflammatory joint, kidney, vessel and bowel diseases, and in neurological and endocrinological autoimmune diseases.

The term "colony stimulating factor" refers to a cytokine responsible for controlling the production of white blood cells. Types include granulocyte colony stimulating factor (G-CSF), macrophage colony stimulating factor (M-CSF), and granulocyte macrophage colony stimulating factor (GM-CSF).

The term "cyclic" as used herein refers to an amino acid sequence that comprises, at least in part, a closed chain. For example, oxidation-reduction of two sulfur-containing amino acids (e.g., cysteine and methionine) located within a suitable bond-forming distance in a given peptide sequence may, under the appropriate conditions, lead the sulfur moieties to form a disulfide (S-S) bridge, which comprises a strong covalent disulfide bond between the sulfhydral groups of these amino acids. According to the present invention, the amino acid sequence of some of the EPO-derived peptides of the present invention contain two cysteines located within a suitable bond-forming distance. Oxidation-reduction of the sulfide groups on each of these cysteines results in the formation of a disulfide bond.

The term "demyelination" as used herein refers to an abnormal process that leads to the loss or breakdown of myelin. In MS, demyelination results in distorted or blocked signals.

The terms "demyelinating disease", "demyelinating condition" or "demyelinating syndrome" are used interchangeably herein to refer to a disease of the nervous system in which the myelin sheath of neurons is damaged, which impairs the conduction of signals in the affected nerves, causing impairment in sensation, movement, cognition, or other functions, depending on which nerves are involved. Some demyelinating diseases are caused by infectious agents, some by autoimmune reactions, and some by unknown factors. Organophosphates, a class of chemicals that are the active ingredients in commercial insecticides, also will demyelinate nerves. Examples of demyelinating diseases include, but are not limited to multiple sclerosis, transverse myelitis, Guillain-Barre syndrome, and progressive multifocal leukoencephalopathy.

One aspect of the present invention provides stabilized EPO-derived peptides. The terms "EPO derived peptide", "EPO AB loop peptide," and "short EPO peptide" are used interchangeably to refer to stabilized short peptides derived from whole molecule EPO according to the present invention. This term includes, but is not limited to, the following peptides, each of whose amino acid sequence is shown from its N-terminal end to its C terminal end:

EPOp2 peptide, whose amino acid sequence is TTGCAEHCSLNENITVPDTK (SEQ ID NO: 1);

JM peptide, whose amino acid sequence is AEHCSLNENITVPDTKVNFYAWRME (SEQ ID NO: 2);

JM-1L peptide, whose amino acid sequence is CAEHCSLNENITVPDTKV (SEQ ID NO: 3);

JM-Obiotin N-peptide, a biotinylated derivative of JM0 peptide (SEQ ID NO: 21, see infra), whose amino acid sequence is d-biotin-AEHCSLNENITVPDTKV (SEQ ID NO: 4)

JM-3S peptide, whose amino acid sequence is CAEHCS (SEQ ID NO: 5);

JM-3L peptide, whose amino acid sequence is GCAEHCSL (SEQ ID NO: 6);

JM-4 peptide, whose amino acid sequence is GCAEHCSLNENITVPDTKV (SEQ ID NO: 7);

JM-4biotin peptide, a biotinylated derivative of JM-4 peptide, whose amino acid sequence is dBiotin-GCAEHC-SLNENITVPDTKV (SEQ ID NO: 8);

JM-5 peptide, whose amino acid sequence is CAEHC-SLNENITVP (SEQ ID NO: 9);

JM-5biotin-N peptide, a biotinylated derivative of JM-5 peptide, whose amino acid sequence is dBiotin-AEHC-SLNENITVP (SEQ ID NO: 10);

JM-6 peptide, whose amino acid sequence is TTGCAE-HCSLNENITVPDTKV (SEQ ID NO: 11);

JM-7 peptide, whose amino acid sequence is TTGCAE-HCSLNENITVP (SEQ ID NO: 12);

JM-14 peptide, whose amino acid sequence is SLNEN-ITVPDTKV (SEQ ID NO: 13);

JMObiotin-C peptide, a biotinylated derivative of JM0 peptide (SEQ ID NO: 21), whose amino acid sequence is AEHCSLNENITVPDTKK-biotin (SEQ ID NO: 14);

BW2L peptide, whose amino acid sequence is: CAEHC-SLNKNINLDSVDGVP ((SEQ ID NO: 15);

BW2biotin peptide, a biotinylated derivative of -hCNTF peptide (SEQ ID NO: 28, see infra), whose amino acid sequence is YVKHQGLNKNINLDSVDGVP-biotin (SEQ ID NO: 16);

BW3L peptide, whose amino acid sequence is GCAE-HCSLMENNLRRPNL (SEQ ID NO: 17);

BW3Lbiotin peptide, a biotinylated derivative of BW3L peptide, whose amino acid sequence is dBiotin-GCAEHC-SLMENNLRRPNL (SEQ ID NO: 18);

BW3biotin-N peptide, a biotinylated derivative of hIL-3 peptide (SEQ ID NO: 29, see infra), whose amino acid sequence is dBiotin-ILMENNLRRPNL (SEQ ID NO: 19);

BW4biotin-N peptide, a biotinylated derivative of a truncated EPO-hIL-3 peptide, whose amino acid sequence is dBiotin-AEHCSLMENNLRRPNL (SEQ ID NO: 20);

JM0 peptide, whose amino acid sequence is AEHC-SLNENITVPDTKV (SEQ ID NO: 21);

JM5biotin-C peptide, whose amino acid sequence is AEHCSLNENITVP-dbiotin (SEQ ID NO: 27);

hCNTF peptide, whose amino acid sequence is YVKHQGLNKNINLDSVDGVP (SEQ ID NO: 28);

hIL-3 peptide, whose amino acid sequence is LMENN-LRRPNL (SEQ ID NO: 29); and

BW4 peptide, whose amino acid sequence is AEHC-SLMENNLRRPNL (SEQ ID NO: 30).

The term "derivative" as used herein refers to an amino acid sequence produced from an EPO-derived peptide either directly or by modification or partial substitution of the EPO-derived peptide. A biotinylated EPO-derived peptide derivative is an EPO-derived peptide to which biotin has been chemically linked.

The term "glial cell" as used herein refers to the connective tissue cells of the central nervous system (CNS), that serve as the supportive structure that holds together and protects neurons.

The term "graft" as used herein refers to a tissue transplanted without a blood supply. The term "graft rejection" as used herein refers to a process by which the immune system of the recipient of a graft attacks the transplanted organ or tissue.

The term "immune-mediated inflammatory network" as used herein refers to cells of the immune system and their specific receptors and products. These include, but are not limited to, major histocompatibilty complex (MHC) class I and class II molecules, chemokines, cytokines, and other molecules that act on specific receptors on, and affect the behavior of, target cells.

The terms "immune response" or the term "immune-mediated" concerning a response as used herein refer to any functional expression of a subject's immune system, against either foreign or self antigens, whether the consequences of these reactions are beneficial or harmful to the subject.

The terms "immunomodulating", immunomodulation, and immunomodulate as used herein refer to changes in the body's immune system, caused by agents that activate or suppress its function.

As used herein the terms "inflammation", "inflammatory" or "immuno-inflammatory" refer to a physiologic response to infection and injury in which cells involved in detoxification and repair are mobilized to the compromised site by inflammatory or immuno-inflammatory mediators. The classic signs of inflammation are pain (dolor), heat (calor), redness (rubor), swelling (tumor), and loss of function (functio laesa). Histologically, inflammation involves a complex series of events, including dilatation of arterioles, capillaries, and venules, with increased permeability and blood flow; exudation of fluids, including plasma proteins; and leukocytic migration into the inflammatory focus.

The term "acute inflammation" as used herein, refers to inflammation, usually of sudden onset, characterized by the classical signs, with predominance of the vascular and exudative processes. The term "chronic inflammation" as used herein refers to inflammation of slow progression, which is marked chiefly by the formation of new connective tissue; it may be a continuation of an acute form or a prolonged low-grade form, and usually' causes permanent tissue damage.

The body's response to inflammation can include various symptoms, including edema, vasodilation, fever and pain, amongst others. For example, when inflammation is localized to joints, swelling of the joint lining, wearing down of cartilage and stiffening of the joints may occur. Thus, inflammation involving joints can be linked to a wide range of underlying joint conditions, from sprains to diseases, disorders and conditions collectively referred to as "arthritis," including rheumatoid arthritis, associated with autoimmune disorders.

Regardless of the initiating agent, the physiologic changes accompanying acute inflammation encompass four main features: (1) vasodilation, which results in a net increase in blood flow, is one of the earliest physical responses to acute tissue injury; (2) in response to inflammatory stimuli, endothelial cells lining the venules contract, widening the intracellular junctions to produce gaps, leading to increased vascular permeability which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The terms "inflammatory" or immuno-inflammatory" as used herein with respect to mediators refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, interleukin-1, interleukin-4, interleukin-6, interleukin-8, tumor necrosis factor (TNF), interferon-gamma, and interleukin 12.

The term "injury" refers to damage or harm caused to the structure or function of the body of a subject caused by an agent or force, which may be physical or chemical.

The term "interleukin" as used herein refers to a cytokine secreted by white blood cells as a means of communication with other white blood cells.

The term "linear" as used herein in the context of a peptide refers to meaning a chain of amino acids arranged in a straight line.

The term "macrophage" as used herein refers to a mononuclear, actively phagocytic cell arising from monocystic stem cells in the bone marrow. These cells are widely distributed in the body and vary in morphology and motility. Phagocytic activity is typically mediated by serum recognition factors, including certain immunoglobulins and components of the complement system, but also may be non-specific. Macrophages also are involved in both the production of antibodies and in cell-mediated immune responses, particularly in presenting antigens to lymphocytes. They secrete a variety of immunoregulatory molecules.

The term "major histocompatibility complex" (MHC) as used herein refers to a complex of vertebrate genes coding for a large family of cell-surface proteins that bind peptide fragments of foreign proteins and present them to T-lymphocytes to induce an immune response. The MHC also plays a role in resistance to infection and in susceptibility to a number of autoimmune diseases. The MHC complex is divided into three subgroups called MHC class I, MHC class II, and MHC class III. MHC class I molecules, which are found on almost every nucleated cell of the body, present peptides derived from cytosolic proteins and/or peptides from infectious agents. The peptides mainly are generated in the cytosol by the proteosome, a macromolecule that degrades intracellular proteins into small peptides that then are released into the cystosol. The peptides are translocated from the cytosol into the endoplasmic reticulum by the Transporter associated with Antigen Processing (TAP), a member of the ABC transporter family, to meet the MHC class I molecule, since the peptide binding site of the MHC class I molecule is in the lumen of the ER. MHC class I molecules generally interact exclusively with.CD8+(cytotoxic) T cells.

SMHC class II molecules are found only on a few specialized cell types, including macrophages, dendritic cells, activated T cells, and B cells, all of which are "antigen-presenting cells" (APCs). The peptides presented by class II molecules are derived from extracellular proteins, which are taken up by the cell from its environment, digested in lysosomes, and bound by the class II MHC molecule before the molecule's migration to the plasma membrane. Class II MHC is mainly concerned with presentation of extracellular pathogens. Class II molecules interact exclusively with CD4+(helper) T cells, which help to trigger an appropriate immune response.

The MHC class III region encodes other immune components, such as complement and cytokines.

The term microglia" as used herein refers to the smallest of the glial cells that can act as phagocytic cells, cleaning up CNS debris. They are considered to be a type of immune cell found in the brain. Microglia are close cousins of other phagocytic cells including macrophages and dendritic cells. Like macrophages, microglia are derived from myeloid progenitor cells from the bone marrow. During embryonic development, these cells migrate to the CNS where they differentiate into microglia.

The term "mimic" refers to an EPO derivative comprising a functional domain of EPO protein and a stabilizing domain of EPO protein (to stabilize the molecule) alone or in combination with another molecule which will produce a biological effect, namely immunomodulation and/or anti-inflammation.

The term "modulate" as used herein means to regulate, alter, adapt, or adjust to a certain measure or proportion.

The term "myelin" refers to a fatty covering insulating nerve cell fibers in the brain and spinal cord. It facilitates the smooth, high-speed transmission of electrochemical messages between the CNS and the rest of the body.

Myelin-oligodendrocyte-glycoprotein ("MOG") is an antigen present in the myelin sheath of the CNS thought to be targeted by the autoimmune T cell response in MS. It can recruit both an encephalitogenic T cell response and a demyelinating B cell response.

The term "$MOG_{35-55}$ peptide" ("$MOG_{35-55}$") refers to a peptide whose amino acid sequence is MEVGWYR-SPFSRVVHLYRNGK (SEQ ID NO: 22). MOG35-55 is a major encephalitogenic determinant recognized by both T cells and demyelinating autoantibodies in MS. The term "$MOG_{40-54}$ peptide" ($MOG_{40-54}$) refers to a peptide whose amino acid sequence is YRSPFSRVVHLYRNG (SEQ ID NO: 23). The term "$MOG_{44-54}$ peptide" ("MOG 44-54") refers to a peptide whose amino acid sequence is FSRVVH-LYRNG (SEQ ID NO: 24).

As used herein, the term "MOG-EAE" refers to myelin-oligodendrocyte-glycoprotein-induced EAE. C57BL/6 mice immunized with native MOG and $MOG_{35-55}$ peptide usually develop a paralytic progressive neurological disease with extensive plaque-like demyelination.

The term "neurological injury" as used herein refers to an injury of, pertaining to, or relating to the nerves and the nervous system comprising the central nervous system and peripheral nervous system).

The term "peptide" as used herein refers to two or more amino acid molecules linked together by a peptide bond so that the alpha carboxyl group of one is bound to the alpha amino group of another.

The term "$PLP_{139-151}$ peptide" refers to a peptide corresponding to amino acids 139-151 of proteolipid protein having the amino acid sequence HSLGKWLGHPDKF (SEQ ID NO: 25).

The term "peripheral nervous system" (PNS) as used herein refers to the cranial nerves, spinal nerves, nerve plexuses, and the spinal and autonomic ganglia associated with them.

The term "red cell indices" refers to indices that help classify red blood cells (RBCs or erythrocytes) as to their size and hemoglobin content. "Hematocrit" (HCT) refers to the proportion of red blood cells as a percentage of total blood volume. A normal hematocrit for human subjects is about 40% to about 55% for men and about 35% to about 45% for women. "Hemoglobin" (HGB) refers to the number of grams of hemoglobin in a deciliter of blood (g/dL). Normal hemoglobin levels in healthy adult human subjects are about 14 g/dL to about 18 g/dL for men and about 12 g/dL to about 16 g/dL for women. As a rough guideline, hemoglobin generally should be about one-third the hematocrit. "Red Blood Cell Count" (RBC) refers to the total number of red blood cells in a quantity of blood. Normal ranges in human subjects are about 4.5 million cells/mm$^3$ to about 6.0 million cells/mm$^3$ for men and about 4.0 million cells/mm$^3$ to about 5.5 million cells/mm$^3$ for women. The term "substantially normal red blood cell indices" means within about 10% of these normal values. Hematocrit, hemoglobin, and red blood cell count are used to calculate the three red blood cell indices: mean corpuscular volume (MCV), mean corpuscular hemoglobin (MCH), and mean corpuscular hemoglobin concentration (MCHC). Mean Corpuscular Volume (MCV) refers to the average size, or volume, of individual red blood cells. Conditions such as iron deficiency can lead to smaller than normal red blood cells, while certain vitamin deficiencies and some drugs (including nucleoside reverse transcriptase inhibitors [NRTIs]) can produce larger than normal cells. Mean Corpuscular Hemoglobin (MCH) and MCH Concentration (MCHC) refer to the amount or concentration, respectively, of hemoglobin in an average red blood cell.

The term "stroke" refers to the sudden interruption of blood supply to a part of the brain either by occlusion (an ischemic or embolic stroke), by hemorrhage (a hemorrhagic stroke) or other causes.

The term "subject" as used herein includes animal species of mammalian origin, including humans.

The term "transplant" refers to the transfer of a whole or partial organ, a tissue, or a cell from a donor site on a subject's body to another site or from the body of one subject to another subject for the purpose of replacing the recipient's damaged or failing organ, tissue or cells with a working organ, tissue, or cell from the donor site.

The term "transplant rejection" as used herein refers to a process by which the immune system of the recipient of a transplant recognize a mismatch of the major histocompatability complex proteins and attacks the transplanted organ or tissue.

The term "traumatic injury" as used herein refers to an unintentional or intentional wound or damage to the body resulting from acute exposure to energy—such as heat or electricity or kinetic energy from a crash or as a normal consequence of surgery—or from the absence of such essentials as heat or oxygen caused by a specific event, incident, or series of events. As used herein the term "treating" includes abrogating, substantially inhibiting, slowing or reversing the progression of a condition, substantially ameliorating clinical or aesthetical symptoms of a condition, substantially preventing the appearance of clinical or aesthetical symptoms of a condition, and protecting from harmful or annoying stimuli.

The term "tumor necrosis factor-alpha" (TNF-α) refers to a cytokine produced by activated macrophages, monocytes, neutrophils and T-cells, that acts as a cytolytic and cytostatic agent.

The terms "whole EPO" and "whole EPO molecule" are used interchangeably to refer to the 165 amino acid glycoprotein hormone erythropoietin.

In one aspect, the present invention provides EPO-derived peptide compositions.

The peptide compositions of the present invention may be administered systemically either orally, buccally, parenterally, by inhalation or insufflation, rectally or topically in dosage unit formulations containing conventional nontoxic pharmaceutically acceptable carriers, adjuvants, and vehicles as desired. The term "adjuvant" as used herein refers to any component which improves the characteristics, efficacy or potency of a formulation, drug or immunological agent. The term "vehicle" refers to a substance that facilitates the use of a drug or other material that is mixed with it.

The compositions of the present invention may be in a form suitable for oral use, for example, as tablets, troches, lozenges, aqueous or oily suspensions, dispersible powders or granules, emulsions, hard or soft capsules or syrups or elixirs. As used herein, the terms "oral" or "orally" refer to the introduction into the body by mouth whereby absorption occurs in one or more of the following areas of the body: the mouth, stomach, small intestine, lungs (also specifically referred to as inhalation), and the small blood vessels under the tongue (also specifically referred to as sublingually). Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient(s) in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled release.

Compositions of the present invention also may be formulated for oral use as hard gelatin capsules, where the active ingredient(s) is(are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

The compositions of the present invention may be formulated as aqueous suspensions wherein the active ingredient(s) is (are) in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also may contain one or more coloring agents, one or more flavoring agents, and one or more sweetening agents, such as sucrose or saccharin.

Compositions of the present invention may be formulated as oily suspensions by suspending the active ingredient in a vegetable oil, for example *arachis* oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Compositions of the present invention may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients, or example, sweetening, flavoring and coloring agents also may be present.

The compositions of the invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or *arachis* oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

For buccal administration, the compositions of the present invention may take the form of tablets or lozenges formulated in a conventional manner.

The compositions of the present invention may be in the form of a sterile injectable aqueous or oleaginous suspension. The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), intrasternal injection, or infusion techniques. A parenterally administered composition of the present invention is delivered using a needle, e.g., a surgical needle. The term "surgical needle" as used herein, refers to any needle adapted for delivery of fluid (i.e., capable of flow) compositions of the present invention into a selected anatomical structure. Injectable preparations, such as sterile injectable aqueous or oleaginous suspensions, may be formulated according to the known art using suitable dispersing or wetting agents and suspending agents.

The sterile injectable preparation may also be a sterile injectable solution or suspension in a nontoxic parenterally acceptable diluent or solvent, for example, as a solution in 1, 3-butanediol. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it doesn't rapidly settle out. In everyday life, the most common suspensions are those of solids in liquid water. Among the acceptable vehicles and solvents that may be employed are water, Ringer's solution, and isotonic sodium chloride solution. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The compositions of the present invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the present invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

The compositions of the present invention may be in the form of suppositories for rectal administration of the composition. "Rectal" or "rectally" as used herein refers to introduction into the body through the rectum where absorption occurs through the walls of the rectum. These compositions can be prepared by mixing the drug with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

The term "topical" refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably. For the purpose of this application, topical applications shall include mouthwashes and gargles.

Topical administration may also involve the use of transdermal administration such as transdermal patches or iontophoresis devices which are prepared according to techniques and procedures well known in the art. The terms "transdermal delivery system", transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for post-menopausal indications, and nicotine for smoking cessation.

Patches suitable for use in the present invention include, but are not limited to, (1) the matrix patch; (2) the reservoir patch; (3) the multi-laminate drug-in-adhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

In some embodiments, the compositions of the present invention may be formulated with an excipient or carrier selected from solvents, suspending agents, binding agents, fillers, lubricants, disintegrants, and wetting agents/surfactants/solubilizing agents. The terms "excipient" or "carrier" refer to substances that do not deleteriously react with the active compounds. Carriers must be of sufficiently high purity and of sufficiently low toxicity to render them suitable for administration to the subject being treated. The carrier can be inert, or it can possess pharmaceutical benefits.

The carrier can be liquid or solid and is selected with the planned manner of administration in mind to provide for the desired bulk, consistency, etc., when combined with an active and the other components of a given composition. Typical pharmaceutical carriers include, but are not limited to, binding agents (including, but not limited to pregelatinized maize starch, polyvinylpyrrolidone or hydroxypropyl methylcellulose); fillers (including but not limited to lactose and other sugars, microcrystalline cellulose, pectin, gelatin, calcium sulfate, ethyl cellulose, polyacrylates or calcium hydrogen phosphate); lubricants (including, but not limited to magnesium stearate, talc, silica, sollidal silicon dioxide, stearic acid, metallic stearates, hydrogenated vegetable oils, corn starch, polyethylene glycols, sodium benzoate, sodium acetate); disintegrants (including but not limited to starch, sodium starch glycolate) and wetting agents (including but not limited to sodium lauryl sulfate). Additional suitable carriers for the compositions of the present invention include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

The term "pharmaceutically acceptable carrier" as used herein refers to any substantially non-toxic carrier conventionally useful for administration of pharmaceuticals in which the active component will remain stable and bioavailable. In some embodiments, the pharmaceutically acceptable carrier of the compositions of the present invention include a release agent such as a sustained release or delayed release carrier. In such embodiments, the carrier can be any material capable of sustained or delayed release of the EPO-AB loop peptide active ingredient to provide a more efficient administration, resulting in less frequent and/or decreased dosage of the active ingredient, ease of handling, and extended or delayed effects. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

The therapeutically active peptides of the present invention can be formulated per se or in salt form. The term "pharmaceutically acceptable salts" refers to nontoxic salts of the peptides of the present invention. The peptide salts which can be used for the invention are pharmaceutically acceptable salts of organic acids or pharmaceutically acceptable salts of inorganic acids. Examples of such pharmaceutically acceptable peptide salts include, but are not limited to, those formed with free amino groups such as those derived from hydrochloric, phosphoric, sulfuric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Additional compositions of the present invention can be readily prepared using technology which is known in the art such as described in Remington's Pharmaceutical Sciences, 18th or 19th editions, published by the Mack Publishing Company of Easton, Pa., which is incorporated herein by reference.

In some embodiments, the compositions of the present invention can further include one or more compatible active ingredients which are aimed at providing the composition with another pharmaceutical effect in addition to that provided by an Epo-AB loop peptide of the present invention. "Compatible" as used herein means that the active ingredients of such a composition are capable of being combined with each other in such a manner so that there is no interaction that would substantially reduce the efficacy of each active ingredient or the composition under ordinary use conditions.

A composition of the present invention, alone or in combination with other active ingredients, may be administered to a subject in a single dose or multiple doses over a period of time. As used herein, the terms "therapeutically effective amount," and "pharmaceutically effective amount" are used interchangeably to refer to the amount of the composition of the invention that results in a therapeutic or beneficial effect, including a subject's perception of health or general well-being, following its administration to a subject.

The concentration of the active substance is selected so as to exert its therapeutic effect, but low enough to avoid significant side effects within the scope and sound judgment of the skilled artisan. The effective amount of the composition may vary with the age and physical condition of the biological subject being treated, the severity of the condition, the duration of the treatment, the nature of concurrent therapy, the specific compound, composition or other active ingredient employed, the particular carrier utilized, and like factors. Those of skill in the art can readily evaluate such factors and, based on this information, determine the particular effective concentration of a composition of the present invention to be used for an intended purpose.

A skilled artisan can determine a pharmaceutically effective amount of the inventive compositions by determining the unit dose. As used herein, a "unit dose" refers to the amount of inventive composition required to produce a response of 50% of maximal effect (i.e. $ED_{50}$). The unit dose can be assessed by extrapolating from dose-response curves derived from in vitro or animal model test systems. The amount of compounds in the compositions of the present invention which will be effective in the treatment of a particular disorder or condition will depend on the nature of the disorder or condition, and can be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, N.Y., 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the present invention are those large enough to produce the desired therapeutic effect. Preferably, the therapeutically effective amount of the compositions of the present invention is administered one or more times per day on a regular basis. A typical dose administered to a subject is between about 250 ng of the composition per kg (of body weight) and about 500 µg of the composition per kg (of body weight).

Those skilled in the art will recognize that initial indications of the appropriate therapeutic dosage of the compositions of the invention can be determined in in vitro and in vivo animal model systems, and in human clinical trials. One of skill in the art would know to use animal studies and human experience to identify a dosage that can safely be administered without generating toxicity or other side effects. For acute treatment, it is preferred that the therapeutic dosage be close to the maximum tolerated dose. For chronic preventive use, lower dosages may be desirable because of concerns about long term effects.

In another aspect, the present invention provides methods of treating symptoms of a disease, disorder or condition having an autoimmune or inflammatory component in a subject in need thereof.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Biologic Activity of Small EPO-Derived Peptides in Mouse Models of EAE Material and Methods:

EPO and Short EPO-Peptide Library and Other Cytokine Mimics:

EPO (Epoetin Alfa, Ortho Biotech products, L.P) in 2,000 U/ml or 10,000 U/ml (1 ml/vial stock) was used for our in vitro and in vivo experiments. EPO-derived small peptides (7-25 amino acids) (SEQ ID NO: 1 through SEQ ID NO: 21, and SEQ ID NO:27 through SEQ ID NO: 30) were synthesized by UMDNJ's Molecular Resource Facility, Invitrogen and United Biochemical Research, Inc., using Fmoc solid phase chemistry on an automated 72-column peptide synthesizer using synthetic amino acids. Quality assurance was performed on peptides by mass spectral analysis and HPLC. The purity of the peptides was >90% by HPLC (table 1). Each purified peptide is shipped with an HPLC document, showing the level of purity, and with a mass spectral analysis. All peptides are lyophilized and sealed under argon to minimize any potential degradation.

Mouse Models of EAE

SJL/J EAE Animal Model:

SJL/J EAE mouse model [Tuohy, V. K., et al., J Immunol, 142: 1523-1527 (1989); Bebo, B. F., Jr., et al., J Immunol, 166: 2080-2089 (2001); Yoshimura, T., et al., J Neurol Sci, 69: 47-58 (1985); Sobel, R. A., et al., J Immunol, 136: 157-163 (1986)] was used to test for protective efficacy of our small EPO-peptides. $PLP_{139-151}$ peptide (HSLGKWL-GHPDKF) [SEQ ID NO: 25] was purchased from Invitrogen Co. The $PLP_{139-151}$ peptide was dissolved in distilled water and emulsified with an equal volume of complete Freund's adjuvant supplemented with 200 µg of M. tuberculosis H37Ra. Mice (at about 6-8 weeks of age) were immunized subcutaneously at the tail base with 100 µl of peptide emulsion containing 100 µg of $PLP_{139-151}$ antigen on day 0 and day 7. Immediately after the first (day 0) and second immunization (day 7), animals received an intravenous injection of 200 ng of Bordetella pertussis toxin in 200 µl PBS. Animals were weighed daily and assessed for clinical signs of EAE by two independent observers. The clinical scoring system used to assess for neurological deficit in our mouse EAE model was: 0-normal, 1-tail drop, 2-mild hind leg weakness, 3-severe hind leg weakness (paralysis), 4-hind leg paralysis plus mild front limb involvement, 5-quadriplegia, 6-moribund or death.

C57/BL MOG-EAE Animal Model:

Another EAE mouse model, C57/BL MOG-EAE, also was used to test for protective efficacy of our small EPO-peptides [Li, W., et al., Ann Neurol, 56: 767-777 (2004); Bernard, C. C., et al., J Mol Med, 75: 77-88 (1997)]. Mice were purchased from Charles River Laboratories and maintained in a conventional facility. The studies were conducted in accordance with the Animal Component of Research Protocol guidelines at the VA Hospital, East Orange, N.J. MOG peptide$_{35-55}$ (SEQ ID NO: 22) was dissolved in distilled water and emulsified with an equal volume of complete Freund's adjuvant supplemented with 4 mg/ml mycobacterium tuberculosis H37Ra. Mice were immunized subcutaneously at the tail base with 100 µl of peptide emulsion containing about 100 µg to about 200 µg of MOG antigen. Immediately after immunization and again on post-inoculation day 2, animals received an intravenous injection of 300 µl of 1 µg/ml Bordetella pertussis toxin (List Biological Laboratories, Campbell, Calif.). Animals were weighed daily and assessed for clinical signs of EAE by two independent observers. The same clinical scoring system used for the SJL/J EAE mouse model to assess neurological deficit was applied to the C57BL6 EAE mouse model [Li, W., et al., Ann Neurol, 56: 767-777 (2004)].

Therapy with Short EPO-Peptides or Whole EPO Molecule:

Both C57 BL6 and SJL/J EAE mouse models were used to determine tissue protective activities by short EPO-derived peptides versus the whole EPO molecule. The peptides were dissolved in PBS (at 1 mg/ml) and kept at −80 C°. The peptides were further diluted with PBS before administration in therapy protocols. Treatment was initiated 24 to 48 hours after animals had developed neurological impairment (clinical score 3-5). Groups of EAE animals (6-10 per group) were treated intravenously (i.v.) with 250 ng/kg (about 5 µg/mouse) of the short EPO-peptides or whole EPO molecule in freshly prepared saline vehicle (about 500U/kg/day) for 9-10 days. Control EAE animals were sham treated with i.v. PBS for the same 9-10 day period.

Comparison of the Effect of Whole EPO Molecule Versus Short EPO-Peptides on Hematocrit in SJL/J Mice:

Groups of five SJL/J female mice at 6-8 weeks were given daily i.v. EPO (about 50 U/kg to about 500U/kg), or short EPO-peptides (about 200 p g/kg to about 500 µg/kg) in PBS, or PBS alone for 9-14 days. Blood was collected weekly for 5 weeks to determine changes in RBC mass by measuring alterations in hematocrit.

Tissue Histology Correlation in Short EPO-Peptides Treated Vs. Controls:

Nervous System Tissue Preparation for Routine Histology and Immunohistochemical Examinations:

Animals were sacrificed at different time points after short EPO-peptide treatment to compare histologic changes to those in control EAE animals. Serum was collected and stored at −80° C. for later analysis. Animals were perfused with 4% paraformaldehyde in 0.1M of phosphate buffer and the cerebrum and spinal cord removed. Hematoxylin and Eosin, or Luxol-Fast Blue/PAS stains were used for the initial neuropathologic examination on paraffin embedded sections. Five-micron paraffin sections were cut from the high cervical, thoracic, and low lumbosacral region of the spinal cord.

Double Immunostaining for MHC Class II Antigen:

Double immunostaining for MHC Class II antigen was performed following our standard protocol. [Li, W. et al., Ann. Neurol. 56: 767-77 (2004) Briefly, seven-micron spinal cord cryosections were post-fixed in cold acetone at −20° C. for 10 min and air-dried. Biotinylated MHC class II antibody was diluted to 2 µg/ml in 2% normal horse serum/PBS and applied overnight at 4° C. After brief PBS washes, slides were incubated with an Avidin-Biotin HRP complex for 30 min followed by detection with a Cy3 Tyramide Signal Amplification fluorochrome (TSA) kit for 15 min at room temperature. The slides then were prepared for colabeling either with GFAP [DAKO, Varpinteria, Calif.] or Isolectin B4 [Sigma, St. Louis, Mo.], an alpha-D-galactopyranosyl-binding isolectin from Bandeiraea simplicifolia seeds, to identify astrocytes and microglia/macrophages, respectively. Following blockade of endogenous peroxidase activity (1% $H_2O_2$ in PBS) for 20 min, the slides were incubated with biotinylated rabbit anti-GFAP antibody diluted 1:400 for 30 min, followed by biotinylated anti-rabbit IgG at room temperature for 30 min, and finally by ABC-HRP for 30 min. For microglia/macrophage detection, Isolectin B4 diluted to 10 µg/ml in 2% normal horse serum/PBS was applied at room temperature for 60 min followed by ABC-HRP for 30 min. Visualization were achieved using the FITC-TSA system. Slides were rinsed in distilled water, mounted and analyzed by fluorescent light microscopy and evaluation by confocal scanning microscopy.

Detection of Blood Brain Barrier Breakdown:

To assess the blood brain barrier (BBB) integrity, we first employed an immunohistochemical staining protocol to detect any serum IgG leakage into the spinal cord parenchyma. Seven-micron frozen sections were incubated for 30 min with a Cy3 goat anti-mouse IgG diluted 1:300 in PBS at room temperature. The slides were rinsed twice in distilled water, mounted and analyzed by florescent light microscopy. We also used serum fibrinogen leakage as a second measure of BBB breakdown. The slides were incubated overnight at 4° C. with goat-anti fibrinogen antibody at a concentration of 2 g/ml in 2% normal horse serum/PBS, washed twice with PBS, and reacted with biotinylated anti-goat IgG antibody for 30 min at room temperature. After a brief wash with PBS, the sections were incubated with ABC-HRP for 30 min at room temperature, washed briefly and reacted with DAB.

Effects of Short EPO-Peptides on Enriched EAE-Specific T Cells and on MHC Class I and Class II Expression of Antigen Presenting Cells (APC) in Tissue Culture.

Production of Enriched EAE-Peptide Antigen Specific T Cells:

Whole T cell populations were collected from spleen and inguinal lymph nodes of EAE mice 5-7 days post second immunization with $MOG_{35-55}$ (SEQ ID NO: 22). Syngeneic antigen presenting cells (APCs) prepared from naïve C57/B6 mice were pulsed with $MOG_{35-55}$ peptide antigen (25 g/ml) at 37° C. before being added to responder cells. The cell mixture was incubated in RPMI medium containing cytokines (0.5 ng/ml IL-2 and 0.16 μg/ml IL-7) at 37° C. for 5-7 days. The EAE T cells were analyzed for CD3 and MHC class I/MOG peptide dimer binding specificity and were further enriched by repeat exposure to APC pulsed with MOG peptide. After 2-3 cycles of stimulation, the enriched MOG-specific T cells were analyzed for CD8, CD4, CD3 and specific MOG-MHC class I dimer binding. Influenza viral $Flu_{58-66}$ peptide, whose amino acid sequence is GIL-GFVFTL (SEQ ID NO: 26),/MHC class I dimer was used as a control for non-specific binding.

Treatment of MOG-Specific T Cells with Short EPO-Peptides:

In vitro enriched MOG-specific T cells were incubated with short EPO-peptides at different concentrations for about 24 to about 144 hrs. Enriched MOG-specific T cells incubated without short EPO-peptides served as the control. Freshly obtained normal spleen APCs pulsed with MOG peptides were then added to the short EPO-peptide treated MOG-T cell cultures or control cultures. Flow cytometry was performed at different time points with FITC conjugated monoclonal antibodies (FITC-Mabs) specific for the T lymphocyte antigens CD-3, CD-4 or CD-8 combined with assessment of staining by phycoerythrin (PE) conjugated MOG-peptide/MHC dimers to determine the level of MOG specific T cells.

Treatment of Non-Specific APC Cells with Short EPO-Peptides:

To determine whether short EPO-peptides had an effect on MHC class I or II expression in APCs and if such an effect influenced the number of MOG-specific T cells, freshly prepared APCs were incubated with short EPO-peptides before addition to MOG-Specific T cell cultures. Flow cytometry was performed using anti-MHC class I and class II antibodies. The number of MOG specific T cells was determined 48-102 hrs after co-culture with short EPO-peptide pre-treated APCs by flow cytometry with FITC-Mabs (anti-CD3, anti-CD4 or anti-CD8) and PE conjugated MOG-peptide/MHC dimers as described above.

Microglia Cell Cultures and MHC Class I and II Expression:

An immortalized microglia cell line (EOC 20) derived from a 10-day-old mouse brain was obtained from the American Type Culture Collection and maintained following the protocol provided. When the EOC-20 cells reached confluence, cells were scraped loose and subcultured at a density of $5 \times 10^4$ cells per well onto Lab-Tek II Chamber Slides containing 8 wells. The cells were pretreated for 24 hours in maintenance media containing log dilutions of EPO (100 to 0.01 units/ml), or short EPO-peptides (100 ng to 0.01 ng/ml) and subsequently challenged with gamma-interferon (INF-γ) 100 U/ml for the next 48 to 72 hours. The cells were harvested in PBS and quickly centrifuged at room temperature. The cell pellet was washed twice with ice-cold PBS buffer and resuspended in 100 μl of buffer. In order to block nonspecific binding, the rat anti-mouse CD16/CD32 (Fc III/II receptor) antibody (diluted 1:50) was added and the cell suspension incubated on ice for 10 min. The suspended cells then were incubated with FITC-conjugated anti-mouse MHC class I or MHC class II antibody (diluted 1:50) on ice for 60 min, washed briefly twice with FACS buffer (PBS buffer supplemented with 1% bovine serum albumin (BSA), reconstituted with about 5p to about 400 μl of FACS buffer, and analyzed by flow cytometry. An IgG2 isotype antibody was used for control in each run. A comparison was made between the number of cells expressing MHC class I or class II antigen after IFN-γ challenge versus challenged cells protected by various concentrations of EPO or short EPO-peptides. Data was analyzed using Histogram Statistics by CellQuest software gated for 10,000 events and the Flowjo analysis program.

Simultaneous Detection of Multiple Cytokines and Chemokines from EAE-Specific T Cell Cultures after EPO or Short EPO-Derived Peptides Exposure:

Luminex technology was used to detect multiple cytokines simultaneously and chemokines within cell culture supernatants. In brief, enriched EAE-specific T cells were washed and resuspended at about $4 \times 10^6$/ml and maintained in RPMI 1640 supplemented with 10% fetal calf serum. The cells were plated into 96 wells (about $4 \times 10^5$/well) containing maintenance media and log dilutions of EPO (about 10 units/ml to about 0.1 units/mil), or short EPO-peptides (about 10 ng/ml to about 0.1 ng/ml). Cells in maintenance media alone served as controls. Cell-free culture supernatants were harvested at 48 and 72 h of treatment, and stored at −80° C. until testing by Luminex assay. Frozen supernatants from cell cultures were thawed rapidly at 37° C., mixed by vortexing, and spun at 10,000×g for 5 min in order to remove any solid particles. Aliquots (50 μl) were combined with coated beads. Commercial kits containing multi-cytokine beads (IL-13, IL-2, IL-4, IL-5, IL-6, IL-10, IL-12, TNFα, IFN-γ and GM-CSF) were run with their own buffers and standards, following directions of the manufacturer. Incubations and washes were performed on 1.2 μm filter membrane 96-well microtiter plates. After the final wash, beads in the 96-well microtiter plate were resuspended (125 μl) and loaded into the Luminex instrument. An acquisition gate was set between 8000 and 13,500 for the doublet discriminator, sample volume was 75 μl, and 100 events/region were acquired. Raw data (mean fluorescence intensity) from all of the bead combinations tested was analyzed with MasterPlex QT quantification software in order to obtain concentration values.

Statistical Analysis:

Data are presented as the mean±SEM. The composite data was analyzed by the Kruskal-Wallis one-way analysis of variants. The Mann-Whitney U test was used to determine the significance of the intergroup difference in EAE clinical scores and duration of maximum neurological deficit. Values of $p<0.05$ were considered significant.

Results

Whole EPO Significantly Increases Blood Hematocrit Level in SJL/J Mice.

During the early stage of EPO-protection experiments (EPO 500U/kg) in SJL/J EAE mice, we observed initial clinical improvement in the EPO-treated group compared to PBS controls. However, half of the EPO-treated EAE mice developed pink-blue colored ear/tails and died suddenly after about 5 to about 6 days of EPO administration (500U/kg). Peripheral blood was collected from the remaining mice. As shown in FIG. 1, we found a significant elevation of hematocrit (72-75% in EPO treated mice versus 50-54% in controls). Whole EPO at different dose levels (about 50 U/kg to about 500U/kg) was tested for its hematopoietic effect in SJL/J mice; all doses above 75U/kg/day for 5-7 days increased the hematocrit level significantly. Long term storage of whole EPO molecule after opening stock vials suppresses neuroprotective effects without depressing hematopoietic effects.

Figure 2:
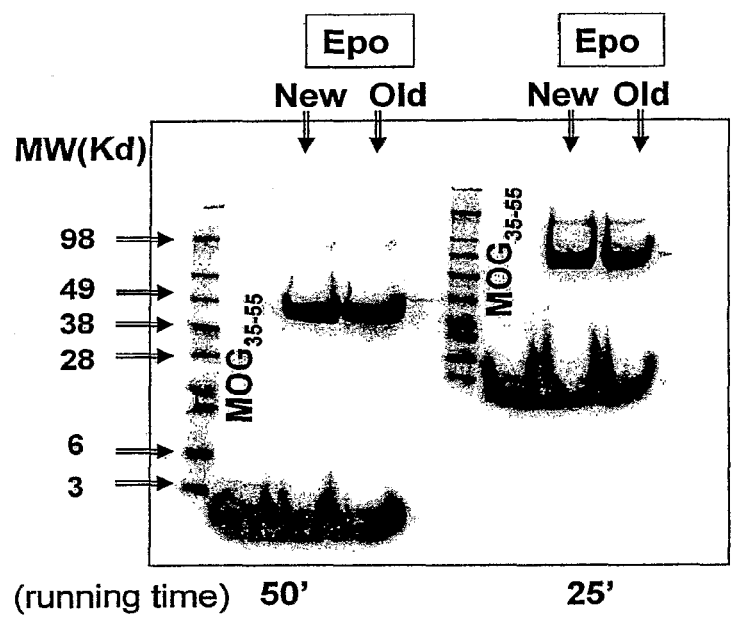
FIG. 2 shows the result of a Western blot assay of newly opened whole EPO and whole EPO opened and stored at 4° C. for about 3 to about 4 weeks.

The whole EPO molecule used in both animal experiments and in vitro cell culture assays (see below) was freshly prepared from the original stock (1 ml/vial) and aliquots usually were kept at 4° C. for one week. The biological activity of the newly opened EPO was compared to that of EPO-aliquots stored at 4° C. for up to 5 weeks. The "old" EPO, i.e., EPO that had been stored at 4° C. for 2-3 weeks after being opened, had greatly decreased neuroprotection and immunomodulating effects. However, when tested for hematopoietic effects, the same "old" EPO still preserved all of its erythropoietic activity on HCT when compared to freshly opened EPO. To be certain that the diminished neuroprotection of the "old" EPO was not caused by gross fragmentation of the whole EPO molecule, the 165 amino acid peptide was analyzed by western blot assay. FIG. 2 shows that both new and old EPO-derived peptides migrate as a single band at about 40 kilodaltons (kD). No fragmentation was observed, even after prolonged running time of the gel (50 min on the left side). These data strongly indicate that while the peptide sequences responsible for tissue protection and hematopoietic biological effects do exist within the full 165 amino acid EPO molecule, the domain that determines the hematopoietic effect is far more biologically stable than the peptide domain responsible for its effects on anti-inflammation and immune modulation.

Development of New EPO-Derived Small Peptides and Other Cytokine Mimics:

Based on our findings as well as on reports from other investigators, we hypothesized that there are at least two distinct functional domains co-existing within the whole EPO molecule and that their distinct biological functions are determined both by their amino sequence and structure. To identify the functional domains and to develop new types of drugs for neuroprotection and immunomodulation, a small peptide library (20 amino acids) derived directly from the whole EPO molecule was made and their biological activity, i.e., the ability to downregulate MHC class I and class II expression on microglial EOC cells tested. A set of short EPO-derived peptides (see Table 1, SEQ ID NO: 1-SEQ ID NO: 14) was created for in vivo and in vitro studies. Peptides were designed to be either linear or partially cyclic by adding a small bicyclic compound d-biotin or cysteine, respectively, to the N- or C-terminal residues. Peptides of different lengths were synthesized in order to determine the precise domain crucial for tissue protection and biological stability. Biotinylated peptides, in addition, were used to locate, isolate and characterize their cognate receptors in tissue or in cultured cells. Other cyclic cytokine mimics (see Table 1, SEQ ID NO: 15-SEQ ID NO: 20) that might have similar biological activity also were created for in vitro and in vivo studies.

Peptides of different lengths were synthesized in order to determine the precise domain that is crucial for tissue protection and biological stability. Biotinylated peptides were similarly prepared in order to locate, isolate and characterize their cognate receptors in tissue or cultured cells. In addition, other cyclic cytokine mimics that might have similar biological functions were invented for in vitro and in vivo studies.

TABLE 1

EPO-derived small peptides and other cytokine mimics:

| Peptide Name | Amino Acid sequence | SEQ ID NO: |
|---|---|---|
| EPOp2 | TTGCAEHCSLNENITVPDTK | 1 |
| JM | AEHCSLNENITVPDTKVNFYAWRME | 2 |
| JM-1L: | CAEHCSLNENITVPDTKV | 3 |
| JM0biotin-N | dbiotin-AEHCSLNENITVPDTKV | 4 |
| JM-3S: | CAEHCS | 5 |
| JM-3L: | GCAEHCSL | 6 |
| JM-4: | GCAEHCSLLNENITVPDTKV | 7 |
| JM-4biotin: | dBiotin-GCAEHCSLLNENITVPDTKV | 8 |
| JM-5: | CAEHCSLLNENITVP | 9 |
| JM-5biotin-N: | dBiotin-AEHCSLNENITVP | 10 |
| JM-6: | TTGCAEHCSLNENITVPDTKV | 11 |
| JM-7: | TTGCAEHCSLNENITVP | 12 |
| JM-14: | SLNENITVPDTKV | 13 |
| JM0biotin-C | AEHCSLNENITVPDTKK-biotin | 14 |
| BW2L: | CAEHCSLKHQGLNKNINLDSVDGVP | 15 |
| BW2biotin: | dBiotin-YVKHQGLNKNINLDSVDGVP | 16 |
| BW3L: | GCAEHCSLMENNLRRPNL | 17 |
| BW3Lbiotin: | dBiotin-GCAEHCSLMENNLRRPNL | 18 |
| BW3biotin-N: | dBiotin-ILMENNLRRPNL | 19 |
| BW4biotin-N: | dBiotin-AEHCSLMENNLRRPNL | 20 |
| JM5biotin-C: | AEHCSLNENITVP-dbiotin | 27 |
| hCNTF: | YVKHQGLNKNINLDSVDGVP | 28 |
| hIL-3: | LMENNLRRPNL | 29 |
| BW4: | AEHCSLMENNLRRPNL | 30 |

Short Cyclic EPO-Peptides Protect Animals Against the PLP-Induced Injury Associated with EAE.

Figure 3:
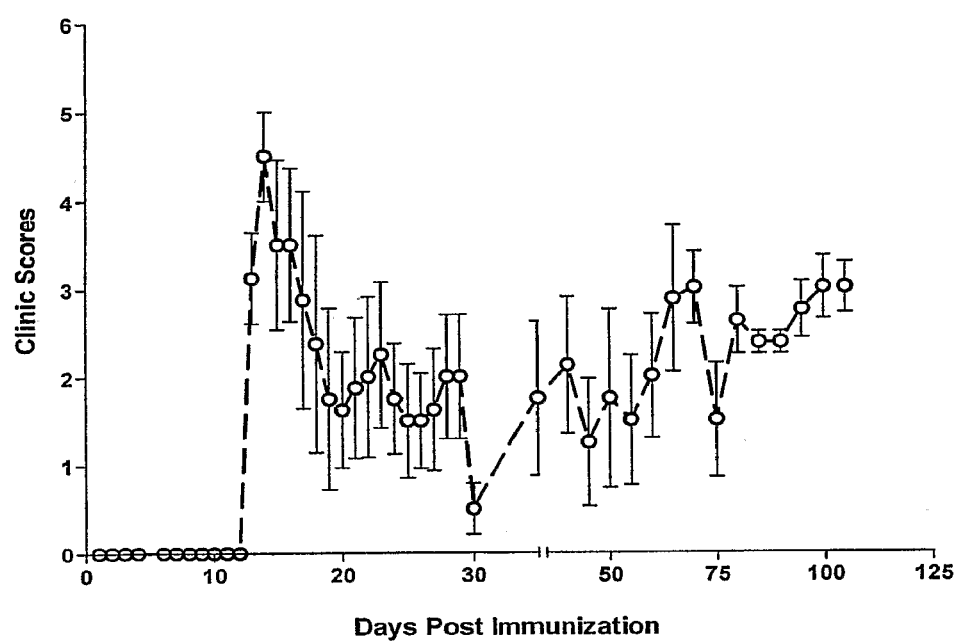
FIG. 3 shows a plot of clinical scores reflecting neurological impairment versus days post immunization in SJL/J mice immunized with PLP.

PLP readily induces EAE in the SJL/J mouse and we observed significant neurologic impairment (clinical score 3-5) about 10 days post-immunization. As shown in FIG. 3, EAE mice showed a relapse and remission pattern that mimics the clinical course seen in MS patients (FIG. 3).

Figure 4:
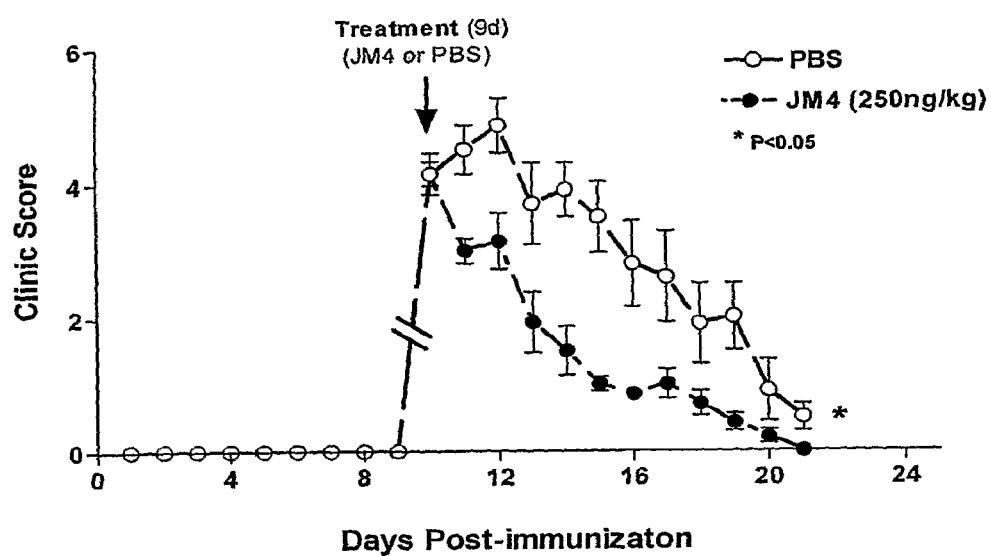
FIG. 4, which is a plot of clinical scores reflecting neurological impairment versus days post immunization in EAE SJL/J mice, shows that short cyclic EPO-derived peptide JM-4 (SEQ ID NO: 7) rapidly reduces the clinical deficit in EAE SJL/J mice.

To determine the therapeutic efficacy of our short EPO-derived peptides, the symptomatic diseased animals were randomly divided into treatment and control groups. FIG. 4 shows one embodiment of the present invention. When mice (n=7-10 per group) were treated i.v. for 10 days with either short EPO-derived peptide JM-4 (SEQ ID NO: 7) (250 ng/kg, daily in 200 µl PBS) or control PBS, dramatic clinical improvement was observed in JM-4 (SEQ ID NO: 7)-treated EAE mice when compared to EAE animals sham treated with saline (p<0.05).

Varied therapeutic efficacy of short linear EPO-derived peptides [JM (SEQ ID NO: 2), JM-14 (SEQ ID NO: 13) AND JM0 (SEQ ID No: 21) initially was observed in the SJL/J EAE mice, but the results varied notably during attempts to confirm the in vivo experiments. In vitro studies also confirmed that the biological activity of these peptides was significantly reduced upon storage (see below) HPLC and sequencing of the peptides demonstrated that these short linear peptides fragmented into many small molecules during the storage. Only freshly prepared linear peptides showed neuroprotective effects. This finding may well explain the lack of progression and enthusiasm in research of EPO-derived small peptides over the last decade since O'Brien et al. [Campana, W. M. et al., Intl J. Mol. Med. 1: 235-41 (1998)] identified the original 17 amino acid linear EPO-derived peptide [Brines, M. and Cerami, A. Nature Reviews (Neuroscience) 6: 484-94 (2005)].

To identify the domains important for both structural and functional stability, a set of small EPO-peptides that contained both linear and cyclic forms was designed by adding a cysteine to the N- or C-terminus of the linear peptides. Biologic activities were retested by assay both in vivo and in vitro.

Figure 5:
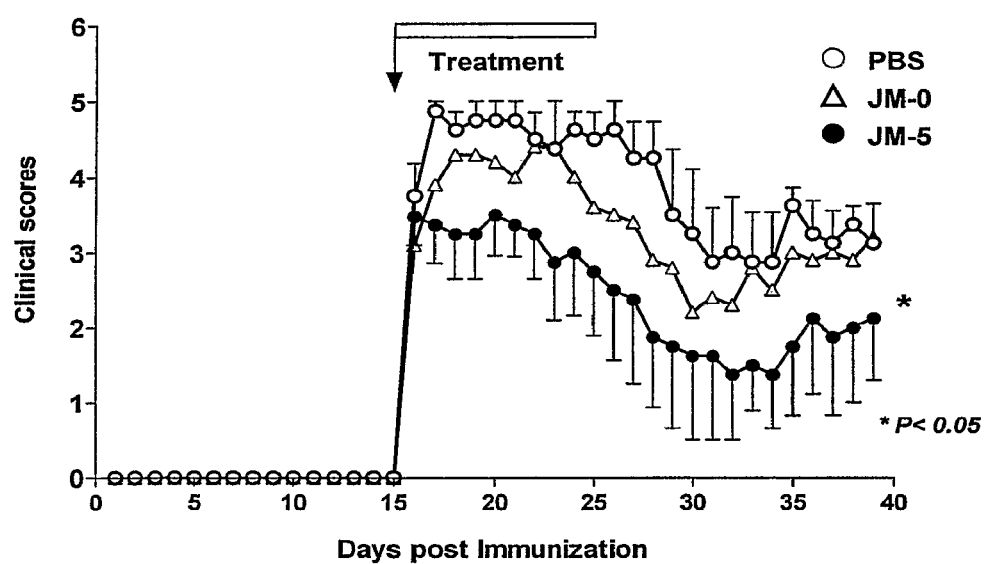
FIG. 5, which is a plot of clinical scores reflecting neurological impairment versus days post immunization in C57/BL6 MOG-EAE mice shows that short cyclic peptide JM-5 (SEQ ID NO: 9) is more effective than linear peptide JM-0 (SEQ ID NO: 21).

In one embodiment of the present invention, the effectiveness of cyclic JM-4 peptide (SEQ ID NO: 7) was compared to that of the linear JM-0 peptide (SEQ ID NO: 21) in a MOG-EAE animal experiment. The results are shown in FIG. 5. MOG-induced EAE in the C57BL/6 mouse predictably showed a disease onset around day 14 post-immunization as we previously demonstrated. Mice usually developed a progressive course of neurological impairment over the subsequent weeks. The symptomatic animals were divided randomly into three groups that received either daily intravenous EPO-derived peptides (JM-4 (SEQ ID NO: 7) or JM-0 (SEQ ID NO: 21)) at 200 ug/kg/day for 14 days) or saline for the same period. As shown in FIG. 5, minor clinical improvement was observed in the JM-0 treated group, but a much more impressive clinical improvement was clearly observed in JM-5 treated EAE animals when compared to JM-0 or saline-treated EAE controls (p<0.05). This experiment has been repeated many times and the data consistently shows that cyclic peptides (e.g., JM-4 (SEQ ID NO: 7) and JM-5 (SEQ ID NO: 9)) were highly effective in reproducibly protecting EAE animals. In other embodiments, cyclic compounds (JM-4 (SEQ ID NO: 7), JM-5 (SEQ ID NO: 9) and JM-7 (SEQ ID NO: 12) showed even more impressive clinical responses after exposure to air or after prolonged storage at −20° C.

In accordance with some embodiments the present invention, the EPO-derived peptides of the present invention comprise at least 6 amino acids having the peptide sequence XAEHYS (SEQ ID NO: 31). In some of these embodiments, X is a first amino acid residue containing a sulfhydral group and Y is a second amino acid residue containing a sulfhydral group. X and Y may be the same or different amino acids. In these embodiments, the sulfhydral group of the first amino acid residue is at an appropriate distance from the sulfhydral group of the second amino acid residue so that it can form a disulfide bond with the sulfhydral group of the second amino acid residue within the peptide sequence, thus stabilizing the peptide. Cyclization of isolated EPO-derived peptides wherein X and Y are cysteine residues was confirmed by MALDI-TOF mass spectrometry.

Examples of peptide embodiments in which X and Y are cysteine include, but are not limited to, EPO-derived peptides having the amino acid sequence SEQ ID NO: 1, SEQ ID NO; 3, SEQ ID NO: 5, SEQ ID NO: 6, SEQ ID NO: 7, SEQ ID NO: 8, SEQ ID NO: 9, SEQ ID NO: 11, SEQ ID NO: 12, SEQ ID NO: 15, SEQ ID NO: 17, and SEQ ID NO: 18.

In other embodiments, the EPO-derived peptide is stabilized by addition of D-biotin to the N- or C-terminal amino acid. Examples of such peptide embodiments include, but are not limited to SEQ ID NO: 4, SEQ ID NO: 10, SEQ ID NO: 14 and SEQ ID NO: 27.

In yet other embodiments, the EPO-derived peptide is stabilized by addition of D-biotin to the N- or C-terminal amino acid and comprises at least 6 amino acids having the peptide sequence XAEHYS (SEQ ID NO: 31), wherein X is a first amino acid residue containing a sulfhydral group and Y is a second amino acid residue containing a sulfhydral group. X and Y can be the same amino acid or different amino acids. In these embodiments, the sulfhydral group of the first amino acid residue is at an appropriate distance from the sulfhydral group of the second amino acid residue so that it can form a disulfide bond with the sulfhydral group of the second amino acid residue within the peptide sequence, thus stabilizing the peptide. In the drawing below, $S^1$ represents the sulfur atom of each such sulfhydral group.

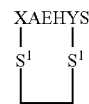

Examples of such peptide embodiments include, but are not limited to, SEQ ID NO: 8.

In other embodiments, the EPO-derived peptide comprises at least 7 amino acids whose sequence is AEHXSLY (SEQ ID NO: 32), wherein X is a first amino acid residue containing a sulfhydral group and Y is a second amino acid residue containing a sulfhydral group. X and Y can be the same amino acid or different amino acids. In these embodiments, the sulfhydral group of the first amino acid residue is at an appropriate distance from the sulfhydral group of the second amino acid residue so that it can form a disulfide bond with the sulfhydral group of the second amino acid residue within the peptide sequence, thus stabilizing the peptide. In the drawing below, $S^1$ represents the sulfur atom of each such sulfhydral group.

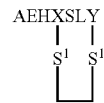

Examples of such peptide embodiments in which X is cysteine and Y is methionine include, but are not limited to SEQ ID NO: 30.

In yet other embodiments, the EPO-derived peptide is stabilized by addition of D-biotin to the N- or C-terminal amino acid and comprises at least 7 amino acids having the peptide sequence AEHXSLY (SEQ ID NO: 32), wherein X is a first amino acid residue containing a sulfhydral group and Y is a second amino acid residue containing a sulfhydral group. X and Y can be the same amino acid or different amino acids. In these embodiments, the sulfhydral group of the first amino acid residue is at an appropriate distance so that it can form a disulfide bond with the sulfhydral group of the second amino acid residue within the peptide sequence, thus stabilizing the peptide. Examples of such peptide embodiments in which X is cysteine and Y is methionine include, but are not limited to SEQ ID NO: 20.

Figure 6:
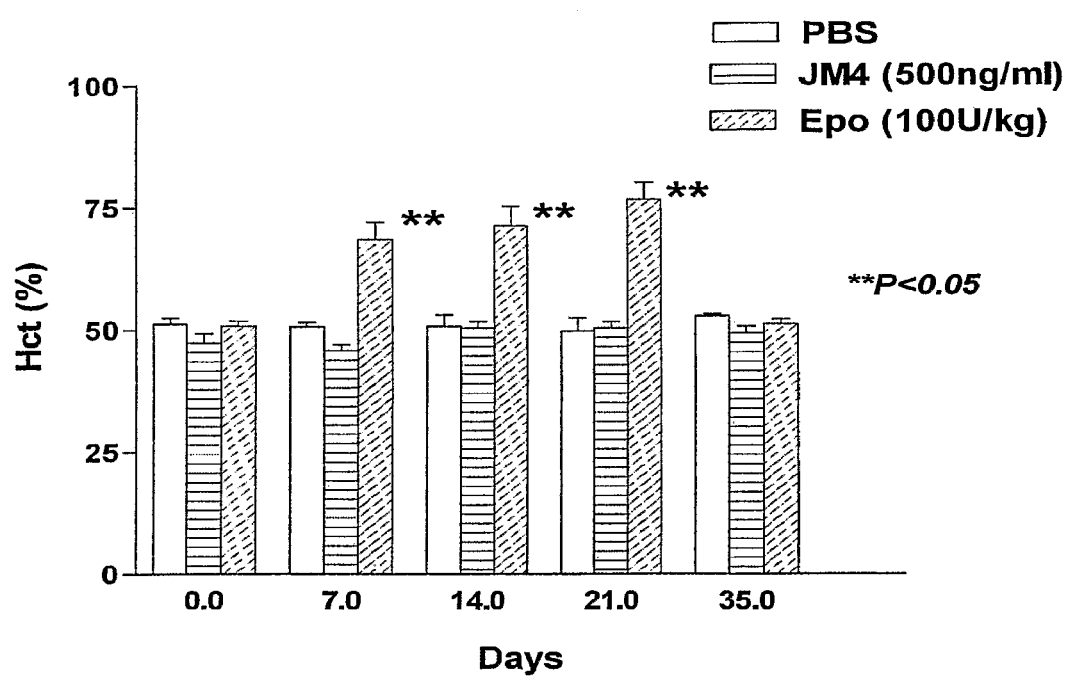
FIG. 6 shows the effect of EPO-derived peptide JM-4 (SEQ ID NO: 7) of the present invention on hematocrit in SJL/J mice.

EPO-Derived Short Peptides do not Increase Hematocrit (HCT) in SJL/i Mice:

To compare the effect of whole EPO to short EPO-peptides on HCT in SJL/J mice, EPO (about 50 U/kg to about 500U/kg), or short EPO-peptides about 250 p g/kg to about 500 p g/kg (approximately 5 µg to about 10 µg per mouse) in PBS were administered i.v. daily to 5 mice per group for 9-14 days. PBS alone was used as a control. Blood was collected weekly for 5 weeks to document changes in HCT. As shown in FIG. 6, the hematocrit in whole EPO treated SJL/J mice increased dramatically within a week of EPO injection and continued to rise to about 75% on day 14. In contrast, the hematocrit in PBS sham-treated or JM peptide treated (JM-35 (SEQ ID NO: 5), JM-3L (SEQ ID NO: 6), JM-4 (SEQ ID NO: 7), and JM-5 (SEQ ID NO: 9)) groups remained unaltered at about 51±1% over a five week follow-up; no deaths or clinical abnormalities occurred in peptide treated groups. The hematocrit in whole EPO-treated animals return to normal levels by day 35 (3 weeks after treatment was completed).

Figure 7:
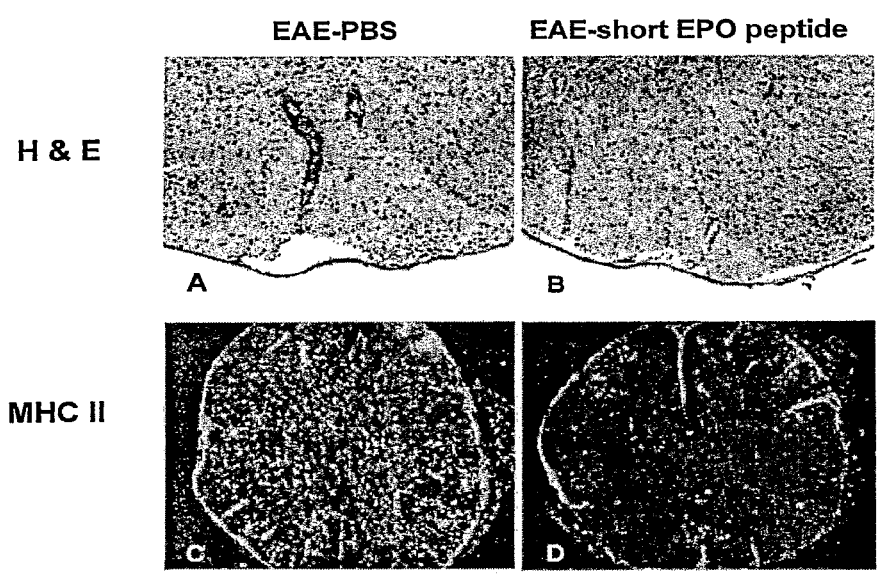
FIG. 7 shows spinal cord sections obtained from EAE animals sacrificed on day 14 after treatment with JM-5 peptide (SEQ ID NO: 9) compared with a saline-treated control. Panels A and B show sections stained with hematoxylin and eosin. Panels C and D shows sections immunofluorescence stained using antibodies against MHC II and glial specific markers.

Treatment with Short EPO-Peptides Results in Axonal Protection and Blocks MHC Class II Expression in EAE Spinal Cord To determine whether or not treatment with short EPO-derived peptides altered histopathological parameters, the spinal cords of EAE mice were examined using H+E staining. As shown in FIG. 7, there was a marked reduction in mononuclear cell infiltration in mice treated with short EPO-peptide JM-1L (SEQ ID NO: 3) as compared to saline-treated controls (FIGS. 7A and 7B). EAE pathology is associated with reactive astroglia and MHC class II expression is even more heightened in EAE activated microglia. To determine whether short EPO-peptide therapy might attenuate glial cell activation in EAE, spinal cord sections were double-labeled immunocytochemically utilizing antibodies against MHC II and glial specific markers. FIGS. 7C and D show spinal cord cryosections obtained from EAE animals sacrificed on day 14 after disease onset. MHC class II expression as expected was markedly upregulated in both central gray and white matter of saline-treated EAE spinal cord when compared to unaffected normal control cord. In striking contrast, the pronounced MHC class II upregulation seen in saline-treated EAE spinal cord was substantially attenuated by short EPO-peptide therapy.

Figure 8:
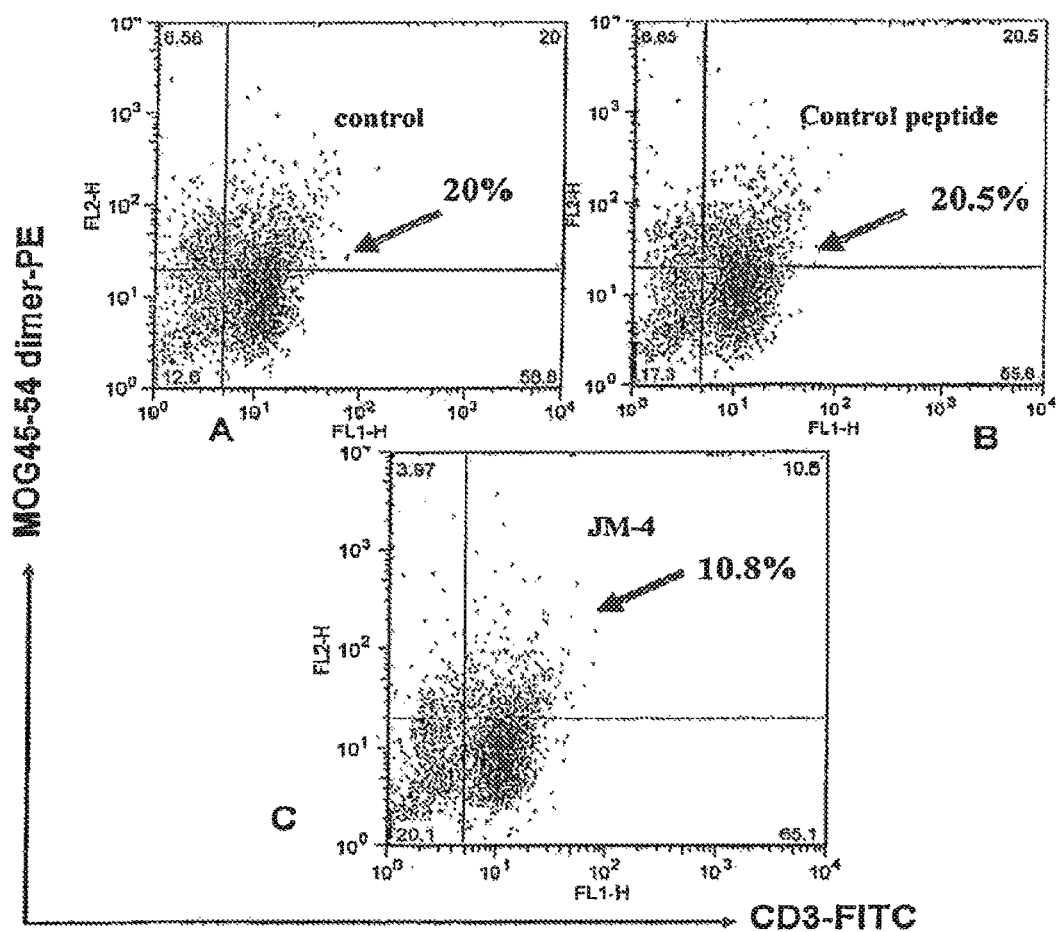
FIG. 8 shows down-regulation of EAE CD3+/MOG 40-54 dimer-double positive T cell populations by EPO-derived peptide JM-4 (SEQ ID NO: 7).

Effects of Short EPO-Peptides on EAE-Peptide Enriched EAE-Specific T Cells:

The pathogenesis of EAE is widely believed to involve T cells. A truncated MOG peptide library derived from $MOG_{35-55}$ (SEQ ID NO: 22) placed in the groove of H-2Db (mouse MHC class I) dimers has been used to identify the key peptide epitopes recognized by pathogenic T cells. Two major MOG peptide epitopes within $MOG_{44-54}$ (SEQ ID NO: 24) were found to be pathogenic for EAE induction. When MOG-specific T cells were transferred into naïve B6 mice, permanent paralysis and extensive CNS demyelination was induced in recipients. To study the effects of our small EPO-peptides on these antigen-specific T cells, in vitro enriched MOG-specific T cells were incubated with short EPO-peptides at different concentrations for about 24 hrs to about 144 hrs. Enriched MOG-specific T cells incubated without short EPO-peptides served as controls. Flow cytometry was performed at different time points with monoclonal antibodies specific for T cell antigens CD3, CD4 or CD8 combined and with MOG-peptide/MHC dimers to determine the level of MOG specific T cells. As shown in FIG. 8, about 20% of EAE-T cells were recognized by both CD3 and MOG40-54 (SEQ ID NO: 23)/MHC class I dimers. When these T cells were treated with short EPO-peptide JM-4 (SEQ ID NO: 7) and JM-4 (SEQ. ID NO: 7) of the present invention for 48-72 hrs, a significant reduction in MOG antigen-specific T cells was observed in samples exposed to the short EPO-peptide treated samples. The irrelevant control peptide had no effect on the MOG antigen-specific T cells population. The effective concentrations of the short EPO-derived peptide JM-4 (SEQ ID NO: 4) used were very low (about 1 ng/ml to about 10 ng/ml).

Figure 9:
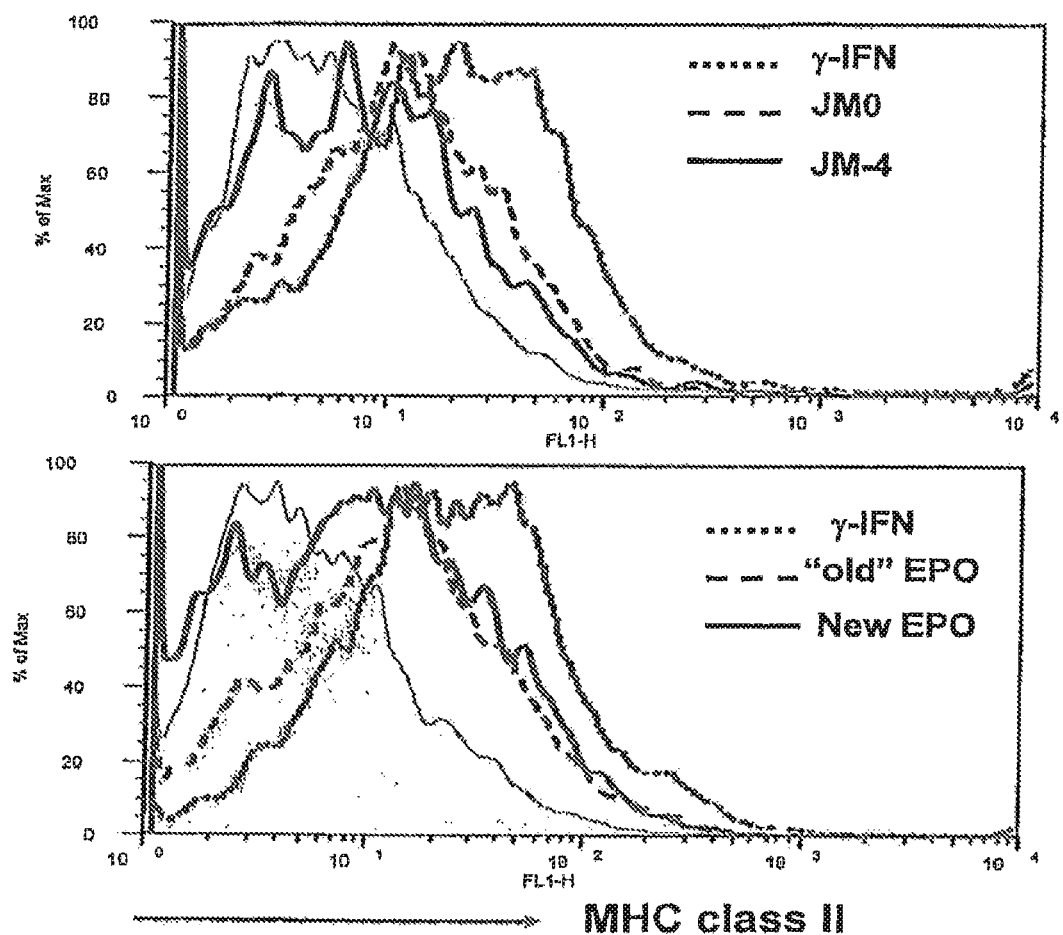
FIG. 9 shows that freshly opened whole molecule EPO and cyclic EPO-derived peptide JM-4 (SEQ ID NO: 7), but neither "old" EPO opened and stored at 4° C. nor linear EPO-derived peptide JM-0 (SEQ ID NO: 21) blocked MHC class II expression in EOC cells.

Freshly Opened Whole Molecule EPO and Cyclic Short EPO-Peptides Derived from Whole Molecule EPO Down-regulate MHC Class II Expression on Activated Microglia An immortalized microglial cell line (EOC 20) derived from a brain of a 10-day-old mouse was used to assess the effect of small EPO-peptides on MHC class I and II expression in cultured microglia. It was found that freshly opened whole molecule EPO and all cyclic EPO-derived peptides [JM-1 L (SEQ ID NO: 3), JM-35 (SEQ ID NO: 5), JM-3L (SEQ ID NO: 6), JM-4 (SEQ ID NO: 7), JM-5 (SEQ ID NO: 9), JM-6 (SEQ ID NO: 11) AND JM-7 (SEQ ID NO: 12)] as well as biotinylated JM0 (SEQ ID NO: 4) of the present invention blocked MHC class II expression in EOC cells, whereas EPO that was opened for previous experiments and stored at 4° C. for about 3 to about 5 weeks or stored linear JM0 peptide (SEQ ID NO: 21) largely failed to block MHC class II expression. FIG. 9 (panels A and B) show that MHC II expression was significantly upregulated when this cell line was challenged with IFN-γ. By staining sister cultures that had been pretreated for 24 hours with peptides before exposure to FN-γ, it was found that both newly opened EPO and the cyclic EPO-peptide JM-4 (SEQ ID NO: 7)) significantly blocked the induction of MHC class II. The effective concentrations of the small EPO-derived peptide were very low (about 1 ng/ml to about 10 ng/ml). In contrast, whole molecule EPO that has been opened and stored for about 2 weeks to about 3 weeks before these experiments ("old EPO") had a much reduced effect in downregulating MHC class II expression in EOC cells. JM-0 (SEQ ID NO: 21), a linear small EPO-derived peptide, demonstrated a variable, much less vigorous effect on MHC class II expression compared to cyclic JM-4 (SEQ ID NO: 7).

Figure 10:
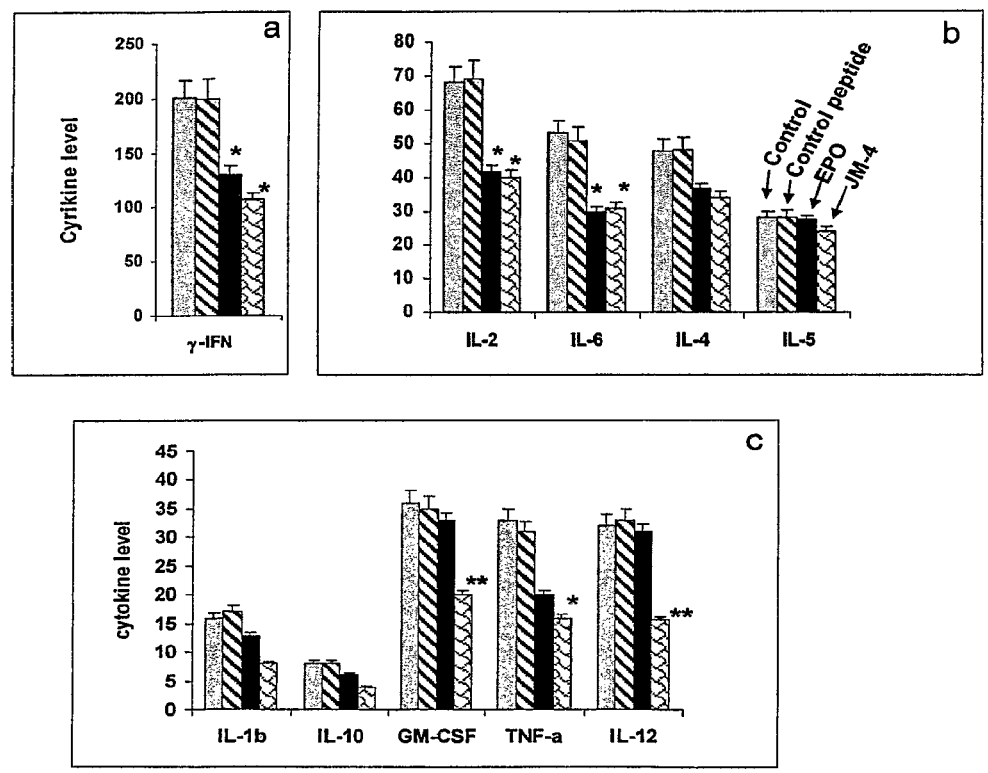
FIG. 10 shows that cyclic EPO-derived peptide JM-4 (SEQ ID NO: 7) suppressed MOG-specific T cell cytokine secretion in MOG-specific T cells.

Small EPO-Peptides of the Present Invention Suppress Cytokine Secretion of EAE-Specific T Cells:

Enriched MOG-specific T cells were exposed to short EPO-peptide JM-4 (SEQ ID NO: 7) at about 1 ng/ml or at about 10 ng/ml for about 48 to about 72 hrs. The culture supernatants were collected for cytokine profile analysis using Luminex technology; the remaining T cells were tested for CD3/MOG peptide dimer positive cell binding as described above. As shown in FIG. 10 (*a-c*), a substantial reduction in levels of major pro-inflammatory cytokines was seen in both JM-4 peptide (SEQ ID NO: 7) treated samples. This correlated with downregulation of the MOG-specific T cell population. An irrelevant control peptide (control 2) had no effect on cytokine level.

Small EPO-Peptides Activate Signal Pathways Differently from Whole Molecule EPO.

According to the general model for JAK/STAT activation, STAT proteins initially are present in inactive forms in the cytoplasm. Following ligand stimulation and receptor dimerization, the JAK/STAT pathway is activated by activation of receptor-bound JAK kinases. These JAK kinases subsequently phosphorylate the receptor at tyrosine residues, which recruits STATs to the receptor. STATs then are phosphorylated to form phosphoSTATs, dimerized and translocated to the nucleus, where the dimers bind to specific sequences in the promoter regions of their target genes, and stimulate the transcription of these genes. (Schindler, et al., Ann. Rev. Biochem. 64: 621-51 (1995)).

Based on the findings from the described in vivo and vitro experiments, the following experiments were performed to determine whether short EPO-derived peptides of the present invention bind to receptors or motifs different from that of whole EPO and thereby activate the same or different signal pathways. UT-7 cells were exposed to either whole EPO (about 1 U/ml to about 10 U/ml) or to JM-4 peptide (SEQ ID NO: 7) (about 1 ng/ml to about 10 ng/ml) for 15 minutes. Activated phophoStat-5 was measured by flow cytometry. The expected induction of Stat 5 by whole molecule EPO (increase of 10% of cells) was found, but there was no induction of stat 5 phosphorylation by JM-4 (SEQ ID NO: 7). Both whole molecule EPO and cyclic JM-4 vigorously induce activation of JAK-2 to a similar degree.

In Vivo Protection of EPO-Derived Peptides in a Stroke Model

Material and Methods:

Mouse Ischemic/Reperfusion Animal Model:

All experiments were carried out on adult male C57BL/6 mice aged 12-15 weeks (28-30 g) (Charles River). Each mouse was anesthetized with an intraperitoneal (i.p.) injection of 0.2 ml of ketamine (20 mg/ml) and xylazine (2.5 mg/ml). The studies were conducted in accordance with the Animal Component of Research Protocol guidelines at the Veterans Administration Hospital, East Orange, N.J.

Infraluminal middle cerebral artery occlusion was produced using a slight modification of a method previously described [McColl, B. W., et al., Brain Res, 997: 15-23 (2004); Belayev, L., et al., Brain Res, 833: 181-190 (1999)]. A midline neck incision was made and the left submandibular gland was freed and retracted laterally. The hyoid bone was exposed, then separated from surrounding connective tissue, muscles and the vagus nerve, and cut in order to better visualize the external carotid artery (ECA) and its distal branches. Particular care was taken to ensure that the vagus nerve was not disturbed. The distal end of the ECA then was ligated with a 5-0 silk suture and divided from the distal branches. At the same time, a second suture was looped around the proximal end of the ECA. After the superior thyroid artery was ligated and divided, the common carotid artery (CCA) was separated from its fascia and the vagus nerve, and the connective tissue surrounding the bifurcation removed. The ECA was then pulled down without disturbing the occipital artery to visualize the proximal portion of the internal carotid artery (ICA). The extracranial branch of the ICA (pterygopalatine artery) and the distal end of the ICA entering the cranial base were both identified so that the direction of the intraluminal thread could be secured.

Prior to the intraluminal thread occlusion, a microvascular aneurysm clip first was placed at the proximal site of the CCA, and then the CCA-ICA axis straightened by gently pulling down the ECA stump with the ligated thread. A 2 cm-long 5-0 nylon monofilament suture, coated with poly-L-lysine that had been rounded with nail polish at the end, then was introduced into an arteriotomy hole-produced with a 30-gauge needle-in the ECA stump. Once the thread was inserted, the looped suture around the ECA was tightened around the inserted intraluminal thread to prevent back flow bleeding from the arteriotomy site. The thread was advanced distally for 10 mm into the ICA to complete the intraluminal occlusion of the middle cerebral artery (MCA). Animals were maintained under anesthesia for 30 min of ischemia, then the intraluminal thread was gently withdrawn. Once the CCA clip was removed, reperfusion started. Finally the suture around the ECA was further tightened, and the skin closed using Auto Clips. Animals were kept on a heat pad until they recovered from anesthesia.

Animals were assessed daily for clinical signs of stroke by two independent blinded observers. The clinical scoring system used to assess for neurological deficit in our stroke model was 0=normal spontaneous movements, 1=mild right-sided hemiparesis with ability to walk, 2=moderate hemiparesis with reduced mobility, 3=severe hemiparesis and immobility with or without spinning behavior, and 4=moribund or death.

JM-4 (SEQ ID NO: 7) Short EPO-Derived Peptide Therapy:

Treatment was initiated within 20 min after the intraluminal thread was withdrawn (reperfusion). JM4 (SEQ ID NO: 7) (7.5 μg) was dissolved in 200 μl of sterile normal saline, and administered intraperitoneally daily for 3 days. Control stroke animals were sham-treated with intraperitoneal saline for the same 3-day period.

Histological Examination:

Animals were sacrificed after 72 hours of reperfusion, or earlier if animals showed signs of a moribund state. Animals were transcardially perfused with 4% paraformaldehyde in 0.1 M phosphate buffer, and the cerebrum was removed. The tissues either were immersed immediately in 4% paraformaldehyde solution and subsequently embedded in paraffin, or were postfixed for 2 hours in 4% paraformaldehyde solution, transferred at 4° C. into 10%, and then 20% sucrose and finally quick frozen in acetone. Hematoxylin and eosin stains were used for the initial neuropathological examination on 5-micron paraffin-embedded sections.

Detection of Blood-Brain Barrier Breakdown:

2% Evans-Blue dye, dissolved in phosphate-buffered saline (200 μl), was administered intravenously 4-5 hours before the animals were sacrificed. Breakdown of the blood brain barrier in the region of the lesion was detected by extravasation of Evans-Blue dye into the brain parenchyma.

Statistical Analyses

The composite data were analyzed by the Kruskal-Wallis one-way analysis of variants. The Mann-Whitney U test (one-tailed) was used to determine the significant of the intergroup differences in clinical score.

Results

JM4 (SEQ ID NO: 7) Effectively Improves Neurologic Deficit in an Intraluminal Occlusive Stroke Mouse Model.

Figure 11:
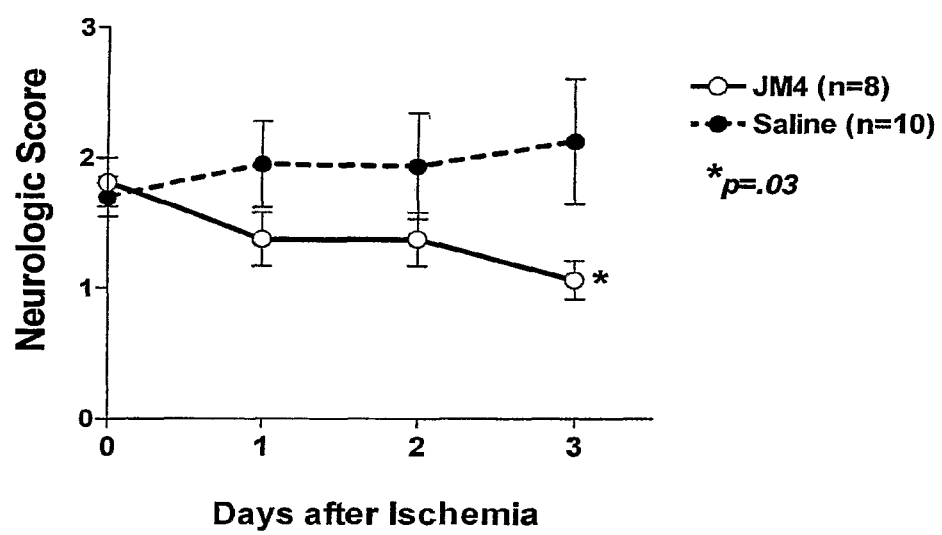
FIG. 11 shows that in a mouse model for acute cerebral ischemia, treatment with EPO-derived peptide JM-4 (SEQ ID NO: 7) substantially improved the neurologic signs of animals after acute cerebral ischemia.

As shown in FIG. 11, in our animal model of ischemic stroke, all animals developed mild to moderate unilateral hemiparesis affecting fore and hind limbs and showed reduced mobility (score 1-2). After a 72 hr reperfusion period, the sham-treated control stroke animals either remained moderately paralyzed or showed increased neurologic deficit. A high mortality rate (25%) was encountered during the early course of the disease in the sham control group. In contrast, JM4 (SEQ ID NO: 7)-treated stroke animals showed substantial improvement in their neurologic deficit and zero mortality was encountered during this observation period.

In Vivo Protection of EPO Short Peptides in a Spinal Cord Injury (SCI) Animal Model:

Material and Methods:

Animal SCI Model:

Experiments were carried out on adult female C57BL/6 mice aged 4-5 months (26-28 g). The studies were conducted in accordance with the Animal Component of Research Protocol guidelines at the Veterans Administration Hospital, East Orange, N.J. Spinal cord injury was performed using a commercially available Infinite Horizon (IH) spinal cord injury device (Precision System & Instrumentation [PSI], Lexington, Ky.). This device creates a reliable contusion injury to exposed spinal cord by rapidly applying a force-defined impact with a stainless steel-tipped impounder [(Engesser-Cesar, C., et al., J Neurotrauma, 22: 157-171 (2005); Scheff, S. W., et al., J Neurotrauma, 20: 179-193 (2003)].

Each mouse was anesthetized with an intraperitoneal injection of 0.15 ml of ketamine (20 mg/ml) and xylazine (2.5 mg/ml) and a laminectomy was performed at the tenth thoracic vertebra (T10). Particular care was taken to ensure that the dura mater was not disturbed during the laminectomy. The exposed spinal column then was stabilized by clamping the rostral T9 and caudal T11 vertebral bodies with serrated Adson forceps (Fine Science Tools [FST]), and the exposed spinal cord was carefully aligned in a horizontal position in order to produce a consistent contusive injury. For this study, all mice received a moderate contusion injury with a 60-kdyne-impact force. Following the injury, force curves were reviewed and the animals with bone hits were excluded from the study. Finally, the wound was irrigated with sterile saline, and the skin openings closed with Auto Clips. Animals were kept on a heating pad until they recovered from anesthesia and bladder expression was performed twice daily until full bladder function was restored.

Animals were assessed daily for clinical signs of spinal cord injury by two independent blinded observers. The clinical scoring system used to assess for neurological deficit in our SCI model was 0=no movement and no weight-bearing, 1=barely perceptible hindlimb movement and no weight-bearing, 2=frequent hindlimb movement and no weight-bearing, 3=occasional stepping and some weight-bearing, 4=mild deficits in hindlimb function, and 5=normal stepping and weight-bearing.

JM-4 Therapy:

Treatment was initiated immediately after spinal cord injury. Small EPO-derived peptide JM-4 (SEQ ID NO: 7) (7.5 µg), dissolved in 200 µl of sterile normal saline was administered intraperitoneally daily for 3 days. Control SCI animal groups were sham-treated with intraperitoneal saline for the same 3-day period.

Statistical Analyses

The composite data were analyzed by the Kruskal-Wallis one-way analysis of variants. The Mann-Whitney U test (one-tailed) was used to determine the significant of the intergroup differences in clinical score.

Results

JM-4 (SEQ ID NO: 7) Effectively Improves Neurologic Deficit in Acute Spinal Cord Injured Mice.

Figure 12:
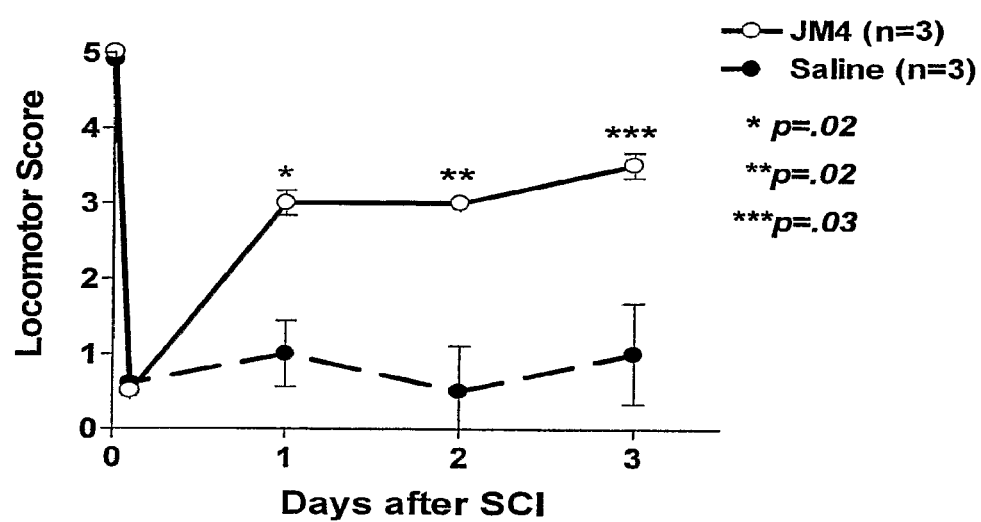
FIG. 12 shows that in a mouse model for acute contusive spinal cord injury, mice treated with EPO-derived peptide JM-4 (SEQ ID NO: 7) showed significant recovery from their neurologic deficit.

In this animal model of contusive SCI, all animals developed complete hindlimb paralysis immediately after the impact. During a 3-day observation period, the sham-treated control SCI animals remained severely paralyzed with little or no ability to stand or walk, whereas JM-4 (SEQ ID NO: 7)-treated SCI animals showed substantial improvement in their neurologic deficit, with 2 of 3 animals regaining ability to walk (see FIG. 12) (p=0.02 on day 1, p=0.02 on day 2, and p=0.03 on day 3; Kruskal-Wallis one-tail analysis).

Table 2 summarizes the data relating to the biological activity, i.e., immunomodulating and tissue protection activity, of the EPO-derived peptides of the present invention in vivo and in vitro. The terms immunomodulating activity and tissue protection activity in turn refer to the ability of the EPO-derived peptides of the present invention to either downregulate MHC class I/II of APCs or to downregulate cytokine secretion or proliferation of EAE-specific T cells, respectively.

In vitro samples were rated on the following scale: −, meaning no biologic activity; + meaning weak biological activity (i.e., <5% downregulation of MHC class I/I or T cells), ++ meaning mild biologic activity (about 5% to about 30% downregulation of MHC class I/II or T cells); +++ meaning moderate biologic activity (about 30% to about 40% downregulation of MHC class I/I or T cells), and ++++ meaning highly effective biologic activity (>about 50% downregulation of MHC class I/I or T cells).

The effect of the EPO-derived peptides of the present invention on the clinical and CNS pathological symptoms of animals suffering from EAE, stroke, spinal cord injury, and arthritis was rated on the following scale: − meaning no effects on clinical and CNS pathological symptoms; ++ meaning mild effects; +++ meaning moderately to highly effective in improving clinical symptoms or CNS pathology; ++++ meaning highly effective on all diseased animals, both clinically and pathologically.

The biological activity of newly synthesized JJM or JM0 linear peptides was variable. Some, but not all, newly constructed JM or JM0 linear peptides showed mild to moderate biological activity. The biological activity of the linear peptides usually disappeared after the peptides were stored is a 1 mg/ml solution in PBS at −20° C. for more than about 2 weeks or after the vials containing the peptide powder were opened for about 2 to about 3 times. In contrast, the biological activity of JM-4 and other cyclic peptides was very stable under the same conditions.

TABLE 2

| Peptide Name | SEQ ID NO: | Immunomodulating/anti-Inflammation Activity | |
|---|---|---|---|
| | | In vitro | In vivo |
| EPOp2 | 1 | +++ | |
| JM | 2 | +/− | +/− (highly variable) |
| JM1L | 3 | +++ | +++ |
| JM0biotin-N | 4 | +++ | |
| JM-3S | 5 | ++ | ++ |
| JM-3L | 6 | ++ | |
| JM-4 | 7 | ++++ | ++++ |
| JM-4biotin | 8 | +++ | |
| JM-5 | 9 | ++++ | ++++ |
| JM-5biotin-N | 10 | +++ | |
| JM-6 | 11 | +++ | |
| JM-7 | 12 | +++ | ++ |
| JM-14 | 13 | ++ | |
| JM0biotin-C | 14 | ++/− | |
| BW2L | 15 | ++ | |
| BW2biotin | 16 | ++ | |
| BW3L | 17 | Not tested | |

TABLE 2-continued

| | | Immunomodulating/anti-Inflammation Activity | |
|---|---|---|---|
| Peptide Name | SEQ ID NO: | In vitro | In vivo |
| BW3Lbiotin | 18 | ++ | |
| BW3biotin | 19 | ++ | |
| BW4biotin | 20 | | |

The degree of tissue protection offered by EPO-derived peptides on diverse forms of injury in non-neural organs is being further determined. Tissue histology is being correlated with clinical findings in EPO-derived peptides treated vs. control animal models.

Whether EPO-derived peptides of the present invention are broadly protective in vivo is being determined in a mouse model of rheumatoid arthritis (collagen induced arthritis). Chick type II collagen (CII) is dissolved at 2 mg/ml in 0.01-0.1M acetic acid. An emulsion prepared by combining the collagen solution 1:1 with Freund's complete adjuvant is prepared by supplementing Freund's incomplete adjuvant with 5 mg/ml *M tuberculosis*. Male DBA/1 mice (8 to 12 weeks) are injected intradermally at several sites around the base of the tail with 100 µl of emulsion containing 150 µg CII. After three weeks, a second antigen booster is administered; mice subsequently become symptomatic between about 5 weeks and about 7 weeks. Symptomatic animals receive five to ten daily intraperitoneal (i.p.) injections of either EPO-derived peptides (about 5 µg to about 10 µg or about 250 ng/kg to about 500 ng/kg) or the same volume of vehicle. The scoring system for evaluating joint disease is based on the criteria of Williams et al: 0=normal, 1=slight swelling and/or erythema, 2=extensive swelling and/or erythema and 3=joint distortion and/or rigidity. The maximum score for four limbs per mouse is 12. Mice are considered to have arthritis when two consecutive positive evaluations have been obtained. Groups of symptomatic animals receive i.v. either EPO-derived peptides of the present invention or control PBS daily for a total of 5-10 days as described in the SJL/J EAE animal protocols previously described. Animals are assessed for redness and swelling of limbs and a clinical score is allocated to each mouse daily for 10 days. Involved joints are evaluated histopathologically for degree of cellular infiltrate, number of TUNEL positive cells and extent of erosion of involved joint surfaces.

In vivo protection by the EPO-derived peptides of the present invention also is being determined in a cardiac tissue injury model. Sprague-Dawley rats (3-4 months of age) are randomly divided into experimental or sham treated groups. Animals are subjected to ligation of the interventricular branch of the left coronary artery under anesthesia (i.p. injection of sodium pentobarbital, 50 µg/kg). Immediately after surgery, half of the animals receive a single i.p injection of EPO-derived peptides of the present invention (100-150 µg) in 0.3 ml of saline. The others receive a single i.p. injection of 0.3 ml of saline at the same time point. Several animals from each group are be sacrificed 24 h after surgery, and their hearts examined by histochemical staining to assess the effect of EPO-derived peptide treatment on the extent of post-myocardial infarction apoptosis (conventional H&E stain, TUNEL reaction for fragmented nuclear DNA and immunohistochemistry for activated caspase 3/9).

To test for the erythropoietic effect of the EPO-derived peptides of the present invention, about 100 µg to about 150 µg (in 0.3 ml of saline, i.p.) are injected into 5-6 naive rats. The same number of animals are injected with 0.3 ml of saline. Blood (0.5 ml) is collected from the jugular vein under pentobarbital anesthesia before treatment and at 4, 7, 14, and 21 days after treatment. The peripheral blood hematocrit in each animal is measured in triplicate for each time point.

Screening of Other Cytokine Mimetic for Tissue Protection:

Other cytokine mimics have been synthesized, including, but not limited to IL-3 and ciliary neurotrophic factor (CNTF), and their tissue protective efficacy is being investigated using the methods described above in a variety of diseased animal models of neural and non-neural organ injury.

Modified forms of EPO are being made that maintain hematopoietic activity without suppressing immune function. Our studies suggest that at least two distinct functional domains (hematopoietic and immunomodulating) exist within the whole EPO molecule. The 15-19mer peptides (JM-5 (SEQ ID NO: 9), JM-4 (SEQ ID NO: 7) or JM-7 (SEQ ID NO: 12)) show significant immunomodulating effects without hematopoietic activity in animals, while the small 7-8mer cyclic EPO-peptide JM-3s (SEQ ID NO: 5) and JM-3L (SEQ ID NO: 6) also have no hematopoietic activity, but retain their immunomodulating effects. Without being limited by theory, the sequence of the cyclic EPO-derived peptides of the present invention is believed to play a dual role: it is important for biologic function and it is critical for maintaining structural stability of the EPO-derived peptides. It is believed that deletion or mutation of the immunomodulating domain (EPO 33-45) will ablate the immune suppression function residing in the whole EPO molecule. This modification will be very important for treatment of cancer patients in that it will avoid unwanted immunosuppression side effects in patients who require EPO therapy for anemia.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A composition comprising an erythropoietin (EPO)-derived peptide, wherein the amino acid sequence of the EPO-derived peptide is the amino acid sequence consisting of SEQ ID NO: 1, SEQ ID NO: 3, SEQ ID NO: 7, SEQ ID NO: 9, SEQ ID NO: 11, SEQ ID NO: 12, SEQ ID NO: 15, SEQ ID NO: 17, or SEQ ID NO: 30.

2. A method of treating a disease, disorder or condition having an inflammatory or autoimmune component in a subject in need thereof, the method comprising administering to the subject a therapeutically effective amount of the composition of claim 1, wherein the composition is effective at ameliorating at least one symptom from at least one disease, disorder, or condition having an inflammatory or autoimmune component.

3. The method according to claim 2, wherein the EPO-derived peptide is at least one of synthetic, non-hematopoietic, cyclic, or combinations thereof.

4. The method according to claim 2, wherein the non-hematopoietic biological activity of the EPO-derived peptide is stable when the peptide is stored at 4° C.

5. The method according to claim 2, wherein the EPO-derived peptide is stabilized by at least one of:

chemically adding a small bicyclic molecule to at least one of the N-terminal end of the peptide, the C-terminal end of the peptide, or both;

a disulfide bond formed between a sulfhydral group of a first amino acid residue and a sulfhydral group of a second amino acid residue along the peptide sequence; or a combination thereof.

6. The method according to claim 5, wherein the disease, disorder, or condition having an inflammatory or autoimmune component is selected from the group consisting of an acute cerebrovascular injury, an acute spinal cord injury, an acute brain injury, an acute cardiovascular injury, an arthritis, an autoimmune disease, a demyelinating disease, a stroke, multiple sclerosis, a neurological injury, and immune-mediated inflammation.

7. The method according to claim 2, wherein the composition is administered by a route selected from the group consisting of orally, buccally, parenterally, nasally, rectally, and topically.

8. The method according to claim 2, further comprising at least one of:

monitoring the subject's red blood cell indices;
maintaining the subject's red cell indices at substantially normal levels during treatment; or
both.

9. The method according to claim 2, wherein the EPO-derived peptide is at least one peptide whose amino acid sequence is SEQ ID NO: 7.

10. The composition of claim 1, wherein the EPO-derived peptide is at least one of cyclic, non-hematopoietic, or both.

11. The composition of claim 1, wherein the composition comprises a therapeutically effective amount of the EPO-derived peptide.

12. The composition of claim 1, wherein the EPO-derived peptide includes a small bicyclic molecule on at least one of N-terminal end of the peptide, the C-terminal end of the peptide, or both.

* * * * *